US011395924B2

(12) United States Patent
McLaughlin et al.

(10) Patent No.: US 11,395,924 B2
(45) Date of Patent: Jul. 26, 2022

(54) IMPLANTABLE DEVICES WITH WELDED MULTI-CONTACT ELECTRODES AND CONTINUOUS CONDUCTIVE ELEMENTS

(71) Applicant: MicroLeads, Inc., Somerville, MA (US)

(72) Inventors: Bryan McLaughlin, Cambridge, MA (US); Girish Chitnis, Watertown, MA (US); John Ogren, Antrim, NH (US)

(73) Assignee: Micro-Leads, Inc., Somerville, MA (US)

( * ) Notice: Subject to any disclaimer, the term of this patent is extended or adjusted under 35 U.S.C. 154(b) by 0 days.

(21) Appl. No.: 16/680,171

(22) Filed: Nov. 11, 2019

(65) Prior Publication Data
US 2020/0215335 A1 Jul. 9, 2020

Related U.S. Application Data

(60) Provisional application No. 62/789,301, filed on Jan. 7, 2019.

(51) Int. Cl.
*A61N 1/375* (2006.01)
*A61N 1/36* (2006.01)
*A61N 1/05* (2006.01)

(52) U.S. Cl.
CPC ......... *A61N 1/3754* (2013.01); *A61N 1/0553* (2013.01); *A61N 1/36125* (2013.01); *A61N 1/3758* (2013.01)

(58) Field of Classification Search
CPC .............. A61N 1/3754; A61N 1/36125; A61N 1/0553; A61N 1/3758
See application file for complete search history.

(56) References Cited

U.S. PATENT DOCUMENTS

| 4,941,961 A | 7/1990 | Noguchi et al. |
| 5,417,719 A | 5/1995 | Hull et al. |

(Continued)

FOREIGN PATENT DOCUMENTS

| CA | 2448912 C | 1/2012 |
| WO | 2007/039735 A1 | 4/2007 |
| WO | 2017/147151 A1 | 8/2017 |

OTHER PUBLICATIONS

International Search Report and Written Opinion for Application No. PCT/US19/68469, dated Mar. 25, 2020 (11 pages).
(Continued)

*Primary Examiner* — Mallika D Fairchild
*Assistant Examiner* — Minh Duc G Pham
(74) *Attorney, Agent, or Firm* — Nutter McClennen & Fish LLP

(57) ABSTRACT

An implantable device has a hermetically sealed enclosure, an electronic device within the hermetically sealed enclosure, and a plurality of feedthrough conductors in mechanical contact with the hermetically sealed enclosure and exposed outside of the hermetically sealed enclosure. The implantable device also has a flexible substrate with a plurality of therapy contacts, and a plurality of continuously conductive elements extending along the flexible substrate from the array of therapy contacts and terminating at a plurality of connection pads. Each of the continuously conductive element is integral with at least one therapy contact and at least one connection pad to electrically communicate the noted therapy contact(s) and the noted connection pad(s). The thickness of each continuously conductive element may be between about 5 and 190 microns. The implantable device also has a plurality of mechanical welded couplings that each couple at least one of the connection pads.

21 Claims, 18 Drawing Sheets

(56) References Cited

U.S. PATENT DOCUMENTS

| | | | |
|---|---|---|---|
| 5,689,877 A | 11/1997 | Grill, Jr. et al. | |
| 6,024,702 A | 2/2000 | Iversen | |
| 6,871,099 B1 | 3/2005 | Whitehurst et al. | |
| 7,012,192 B2 | 3/2006 | Stevenson et al. | |
| 7,142,909 B2 | 11/2006 | Greenberg et al. | |
| 7,211,103 B2 | 5/2007 | Greenberg et al. | |
| 7,613,524 B2 | 11/2009 | Jordan | |
| 7,697,995 B2 | 4/2010 | Cross, Jr. et al. | |
| 7,749,608 B2 | 7/2010 | Laude et al. | |
| 7,846,285 B2 | 12/2010 | Zhou et al. | |
| 7,877,866 B1 | 2/2011 | Greenberg et al. | |
| 8,000,804 B1 | 8/2011 | Wessendorf et al. | |
| 8,805,542 B2 | 8/2014 | Tai et al. | |
| 9,002,459 B2 | 4/2015 | Lee et al. | |
| 9,095,699 B2 | 8/2015 | Rosenberg et al. | |
| 9,174,038 B2 | 11/2015 | Schuttler et al. | |
| 9,364,660 B2 | 6/2016 | Howard et al. | |
| 9,387,326 B2 | 7/2016 | Moffitt | |
| 9,409,023 B2 | 8/2016 | Burdick et al. | |
| 9,561,363 B2 | 2/2017 | Skubitz et al. | |
| 9,572,976 B2 | 2/2017 | Howard et al. | |
| 9,656,085 B2 | 5/2017 | Moffitt et al. | |
| 2003/0233133 A1* | 12/2003 | Greenberg | H05K 3/361 607/36 |
| 2006/0257672 A1 | 11/2006 | Horikoshi et al. | |
| 2007/0207569 A1 | 9/2007 | Greenberg et al. | |
| 2011/0238145 A1* | 9/2011 | Swanson | H01R 24/58 607/116 |
| 2011/0270067 A1 | 11/2011 | Faraji et al. | |
| 2011/0270350 A1 | 11/2011 | Feler et al. | |
| 2012/0006793 A1 | 1/2012 | Swanson | |
| 2012/0245449 A1 | 9/2012 | Williams et al. | |
| 2013/0060313 A1 | 3/2013 | Cross, Jr. | |
| 2013/0345780 A1 | 12/2013 | Tabada et al. | |
| 2014/0039241 A1 | 2/2014 | Jarvik | |
| 2014/0128954 A1 | 5/2014 | Schuttler et al. | |
| 2014/0172051 A1 | 6/2014 | Pannu et al. | |
| 2014/0180361 A1 | 6/2014 | Burdick et al. | |
| 2014/0180370 A1 | 6/2014 | Romero | |
| 2014/0254124 A1 | 9/2014 | Raje et al. | |
| 2016/0007874 A1 | 1/2016 | Ma et al. | |
| 2016/0158559 A1 | 6/2016 | Greenberg et al. | |
| 2016/0192524 A1 | 6/2016 | Ruben | |
| 2016/0213917 A1 | 7/2016 | Dalm et al. | |
| 2016/0254080 A1 | 9/2016 | Shah et al. | |
| 2017/0120056 A1 | 5/2017 | Woods et al. | |
| 2017/0157390 A1 | 6/2017 | Howard et al. | |
| 2017/0246452 A1 | 8/2017 | Liu et al. | |
| 2018/0126155 A1 | 5/2018 | McLaughlin et al. | |
| 2018/0200505 A1 | 7/2018 | McLaughlin et al. | |
| 2018/0213665 A1 | 7/2018 | Dittmer et al. | |

OTHER PUBLICATIONS

International Search Report—International Application No. PCT/US17/60408, dated Jan. 18, 2018, together with the Written Opinion of the International Searching Authority, 12 pages.

International Search Report—International Application No. PCT/US18/14566 dated Mar. 29, 2018, together with the Written Opinion of the International Searching Authority, 13 pages.

Schuettler et al.—Fabrication of implantable microelectrode arrays by laser cutting of silicone rubber and platinum foil*, http://iopscience.iop.org/article/10.1088/1741-2560/2/1/013/pdf, Journal of Neural Engineering, Institute of Physics Publishing, vol. 2, No. 1, Feb. 22, 2005, pp. S121-S128.

Schuettler et al.—Stretchable Tracks for Laser-Machined Neural Electrode Arrays, 31st Annual International Conference of the IEEE EMBS, Minneapolis, MN, USA, Sep. 2-6, 2009, pp. 1612-1615.

Supplementary European Search Report for European Application No. EP 17866496.7, dated Jun. 3, 2020 (9 pages).

* cited by examiner

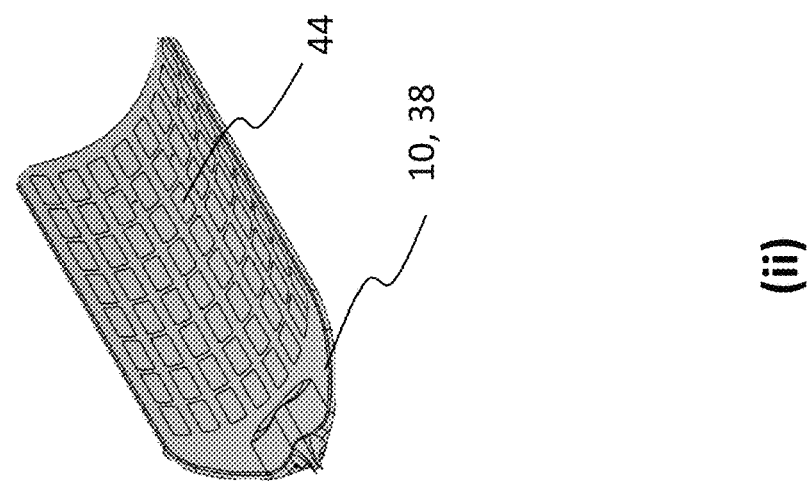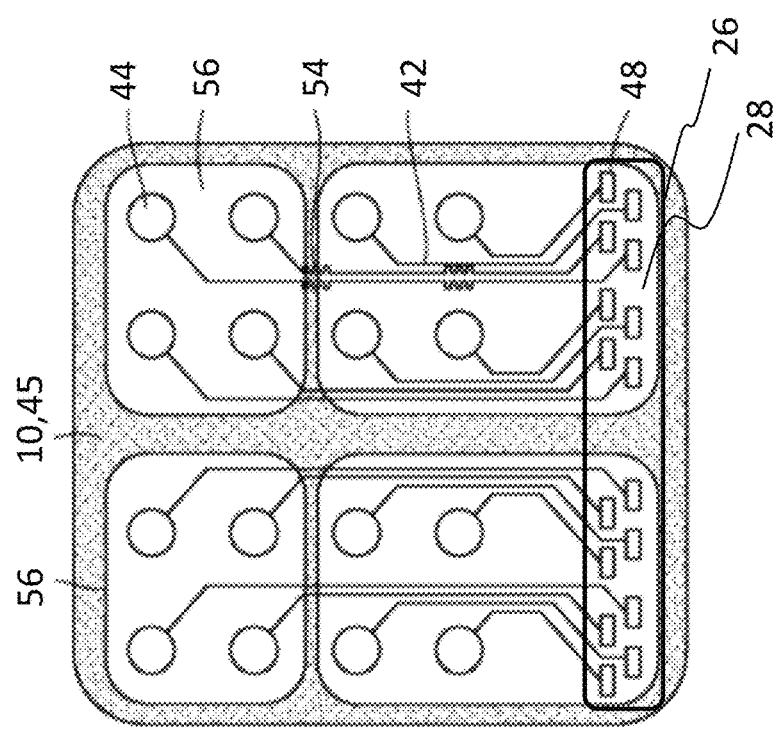
FIG.6

IMPLANTABLE DEVICES WITH WELDED MULTI-CONTACT ELECTRODES AND CONTINUOUS CONDUCTIVE ELEMENTS

This patent application claims priority from provisional U.S. patent application No. 62/789,301, filed Jan. 7, 2019, entitled, "IMPLANTABLE DEVICES WITH MULTI-CONTACT ELECTRODES AND EMBEDDED CONTINUOUS CONDUCTIVE ELEMENTS," and naming Bryan McLaughlin, Girish Chitnis, and John Ogren as inventors, the disclosure of which is incorporated herein, in its entirety, by reference.

FIELD OF THE INVENTION

Illustrative embodiments of the invention generally relate to implantable devices with attached electrode arrays and, more particularly, some embodiments of the invention relate to implantable neural electrodes for neurostimulation or similar devices.

BACKGROUND OF THE INVENTION

Implantable stimulation devices are following a miniaturization trend and new generation devices require additional electrodes to improve therapy. Among other things, such implantable devices may be used to treat conditions of the human body, such as spinal cord stimulation for chronic pain, bladder function, brain stimulation, motor function and autonomic nerve stimulation for organ function. Increasing miniaturization and increasing electrodes, however, present a number of challenges.

SUMMARY OF VARIOUS EMBODIMENTS

In accordance with one embodiment, an implantable device has a hermetically sealed enclosure, an electronic device within the hermetically sealed enclosure, and a plurality of feedthrough conductors integrated with the hermetically sealed enclosure and exposed outside of the hermetically sealed enclosure. The plurality of feedthrough conductors are electrically connected with the electronic device within the hermetically sealed enclosure. The device also has a multi-contact electrode array formed from a flexible biocompatible substrate having a plurality of therapy contacts, and a plurality of continuously conductive elements extending along the flexible substrate from the plurality of therapy contacts and terminating at a plurality of connection pads.

At least one continuously conductive element is integral with at least one therapy contact and at least one connection pad to electrically couple the at least one therapy contact and the at least one connection pad. Preferably, the continuously conductive elements are electrically isolated from one another. Moreover, each conductive element has an element thickness (in a direction generally normal to the substrate) and at least a portion of at least one of the conductive elements has an element thickness of between about 5 microns and about 190 microns. The device further has a plurality of welded couplings connecting at least one of the connection pads to at least one of the feedthrough conductors.

The plurality of continuously conductive elements may include a weldable biocompatible conductor (e.g., noble metals that are stable materials under stimulation in the implanted environment), including one or more of platinum, platinum-iridium, stainless steel, palladium, and rhodium. In one embodiment, noble metals may be formed by laser processing a continuous sheet of conductive material to create the desired features. In another embodiment, the noble metals may be formed from powder, conductive epoxy, conductive ink, electrodeposition, or other deposited materials. The therapy contacts, continuously conductive elements, and connection pads may be considered to form a plurality of connection sets. As such, each connection set may include at least one therapy contact, at least one continuously conductive element, and at least one connection pad. As with other embodiments, each set can be electrically isolated from other connection sets.

The substrate can be formed from a variety of flexible materials, such as at least one insulating material with a modulus of elasticity of between 1 megapascal and 5 gigapascals. Each welded coupling may include a conductive joint formed from at least one pad and at least one feedthrough conductor. In some such embodiments, at least one pad is in electrical contact with at least one continuously conductive element at the conductive joint. It is preferable to form the continuously conductive element material and the feedthrough material from the same material, though different materials may be used to form a composite material bond.

The insulating substrate has a plurality of layers of continuously conductive elements, therapy contacts, connection pads, and a plurality of conductive welded couplings. For example, the substrate may be formed from one or more of silicone, polyurethane, silicone-polyurethane co-polymer, liquid crystal polymer, polyethylene terephthalate, silicone-polyurethane copolymer, parylene, or polyimide. The substrate also may include an insulating material configured to electrically insulate the plurality of continuously conductive elements (e.g., a coating or other material).

Moreover, the hermetically sealed enclosure has a surface through which the plurality of feedthrough conductors extend. In some embodiments, the feedthrough conductors extend beyond the surface of the enclosure. In other embodiments, the plurality of feedthrough conductors are generally flush with the surface of the enclosure.

For robustness, the continuously conductive elements may include metal traces integrated into the substrate. Those skilled in the art may select an appropriate number of therapy contacts. For example, the device may have no fewer than 16 therapy contacts but no more than 72 therapy contacts. Other embodiments, however, may have fewer (e.g., 4 contacts) or more (e.g., 512 contacts). The element thickness of each continuously conductive element may be selected to be uniform or non-uniform (e.g., between about 1 micron and about 125 microns).

To communicate with other devices, the electronic device may have an interfacing portion to electrically couple with an implantable circuit. To that end, the device may have a circuit (e.g., an active device, such as a signal generator, or a passive device) operatively coupled with the hermetically sealed enclosure. Among other things, the implantable circuit housing a pulse generator, switching circuit, memory, processor, and/or wireless telemetry. The device further may have an insulative underfill between adjacent continuous conducting elements.

In accordance with another embodiment, a method of forming an implantable device provides a multi-contact electrode array comprising flexible biocompatible substrate having a plurality of therapy contacts, a plurality of connection pads, and a plurality of continuously conductive elements extending from the plurality of therapy contacts and terminating at the plurality of connection pads. At least one continuously conductive element is integral with the substrate and electrically isolated from other continuously conductive elements, and at least a portion of each continuously conductive element has an element thickness (in a direction generally normal to the substrate) of between about 5 microns and about 190 microns.

The method then contacts the flexible substrate with a hermetically sealed enclosure having 1) an electronic device and 2) a plurality of feedthrough conductors extending from the interior of the hermetically sealed enclosure and exposed outside of the hermetically sealed enclosure. The plurality of feedthrough conductors are in electrical communication with the electronic device within the hermetically sealed enclosure. The method then welds the plurality of connection pads with the plurality of feedthrough conductors to form a set of mechanical welded couplings configured to provide a mechanical and electrical connection between the pads and feedthrough conductors.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 6(i) shows a top view of a flexible, multi-contact therapy array with electrical stimulation contacts, interconnects, contacts for bonding, and a hermetic enclosure. FIG. 6(ii) shows the flexible nature of the multi-contact therapy array.

DESCRIPTION OF ILLUSTRATIVE EMBODIMENTS

In illustrative embodiments, an implantable device is more robust and can be formed from a hermetic device and a thin, flexible electrode substrate. To those ends, the implantable device is formed with a substrate having continuous conductive elements that electrically connect therapy contacts with feedthrough conductors extending from a hermetic enclosure. Despite the continuous conductive elements' relative thinness (e.g., between about 5 microns and about 200 microns), they are configured to mechanically couple with the feedthrough conductors via a welded joint. Details of various embodiments are discussed below.

Active implantable systems provide therapy for a wide range of neurological, motor deficit, and cardiac diseases. For example, neurostimulator devices include spinal cord stimulation for the treatment of chronic pain, peripheral nerve stimulation for treatment of chronic pain, deep brain stimulation for depression or Parkinson's, and vagus nerve stimulation for epilepsy, or nerve stimulation for overactive bladder or urinary incontinence.

Figure 1:
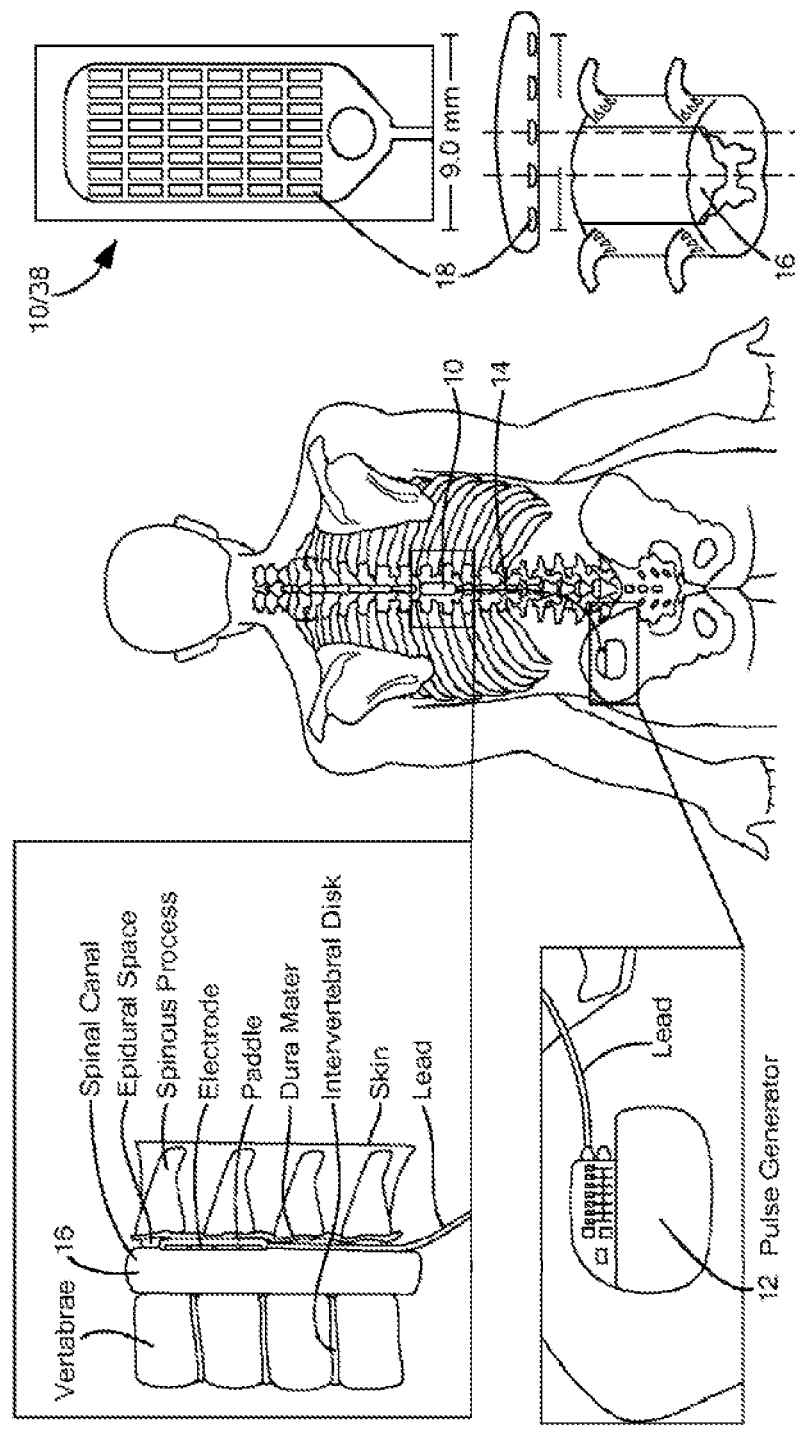
FIG. 1 schematically shows one example of an implantable pulse generator and a multi-contact therapy lead positioned in the body that may be configured in accordance with illustrative embodiments of the invention.

In spinal cord stimulation, an implantable signal generator (e.g., an implantable pulse generator) generates therapeutic pulses or waveforms for delivery through a therapy array/electrode array placed near the spinal cord, dorsal columns, dorsal horn, dorsal roots, dorsal rootlets, or dorsal root ganglia. FIG. 1 schematically shows an example of one use of an implantable pulse generator ("IPG") 12 and electrode array 10 that may be configured in accordance with illustrative embodiments of the invention. For more clarity, FIG. 1 shows the IPG 12 and electrode array 10 outside of the body.

Figure 2:
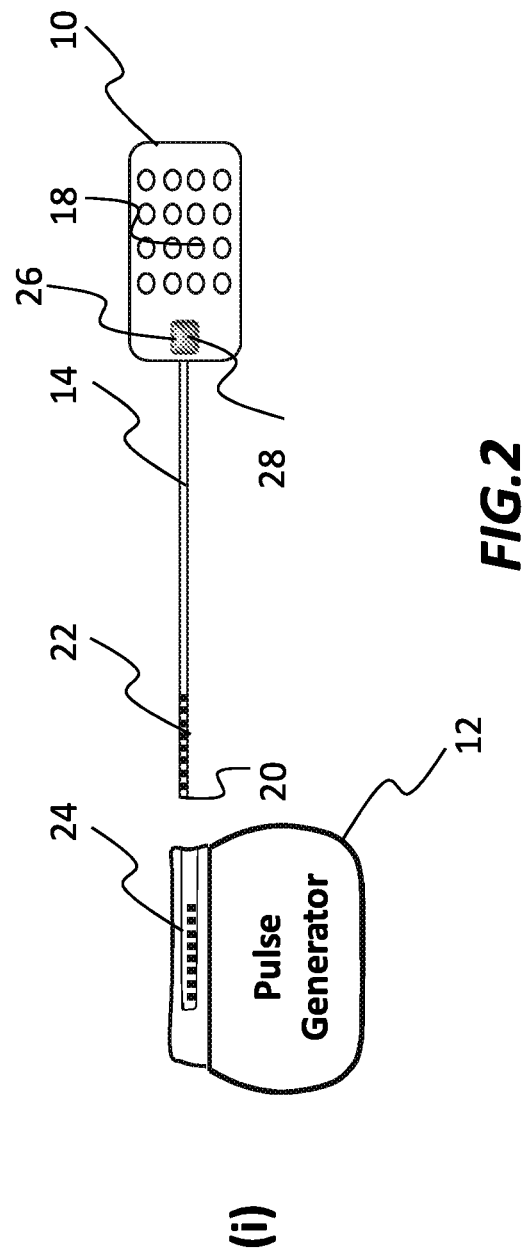
FIG. 2 schematically shows a pulse generator and a flexible electrode array containing a hermetic enclosure with active electronics that may be assembled, bonded, and configured for therapy delivery in accordance with illustrative embodiments of the invention.

As shown, FIG. 1 depicts an exemplary implantable therapy system with the noted IPG 12 to generate pulses, a lead body 14 coupled with the IPG 12, and an implantable therapy array/electrode array 10 with stimulation electrode sites 18. During use, the lead body 14 may be positioned in the epidural space around the spinal cord 16 so that each stimulation contact 18 may deliver therapy to a unique spatial location of the spinal cord 16. The lead body 14 acts as an extension for a proximal connector plug 20 and cylindrical ring contacts 22, which plug into a port plug 24 on the IPG 12 (FIG. 2). Multi-contact electrode arrays 10 may be formed into a variety of geometries, including a peripheral nerve cuff, spiral cuff, deep-brain cylindrical array and, paddle electrode arrays, etc.

Multi-contact electrode arrays provide the ability to deliver therapy over a greater surface area (assuming the same electrode contact size and spacing) and to smaller tissue volumes in a more selective and focused fashion to improve outcomes with fewer off-target effects. Among other things, a greater number and increased density of electrodes has improved resolution for restoration of vision in the retina. For example, one benefit of electrodes over a larger surface with greater density on the surface of the brain is the ability to record or stimulate from the sensory and motor cortex or multiple regions for epilepsy.

Among other things, high-density and greater surface area electrodes in the spine can be used to provide access to a greater number of pain dermatomes from different vertebral levels or at distinct locations across the spinal cord. In cardiac tissue, tissue electrical maps may be created to inform provide greater insight in preparation for selective ablation procedures. Other tissues may also be stimulated including cortical, ganglia, cardiac, parasympathetic nerves, sympathetic nerves, and peripheral nerves. In another embodiment, stimulation of the spinal cord may enhance or reduce function of bladder (micturition and voiding).

Electrode arrays may perform both a therapeutic stimulation function, as well as obtain information from the tissue in a recording fashion that may be used to inform decision making algorithms in the device to deliver an optimized dose of therapy. For example, electrode arrays may couple stimulation therapy to neural or other tissues or record electrical activity from a physiological process (e.g., respiration, gait, muscle contraction), including activity of the nervous system. Electrodes may be connected to the IPG 12 electronics, recording or sensing circuitry and/or multiplexing electronics directly or by means of the lead-body 14 of conductors, which span the distance between the location where the therapy may be delivered and the location where the pulse generator may be positioned to facilitate charging.

As shown in FIG. 2, the IPG 12 may have one or more noted connector ports 24 to facilitate the attachment of a lead 14. As noted above, the multi-contact electrode array 10 contains ring contacts 22 on the connector plug 20 on the lead body 14, and stimulation contacts 18 on the external surface/over a flexible surface. The lead 14 also contains a hermetic sealed enclosure 26 containing an "on-board" electronic device 28 (e.g., a multiplexer, stimulator, etc.).

Figure 3:
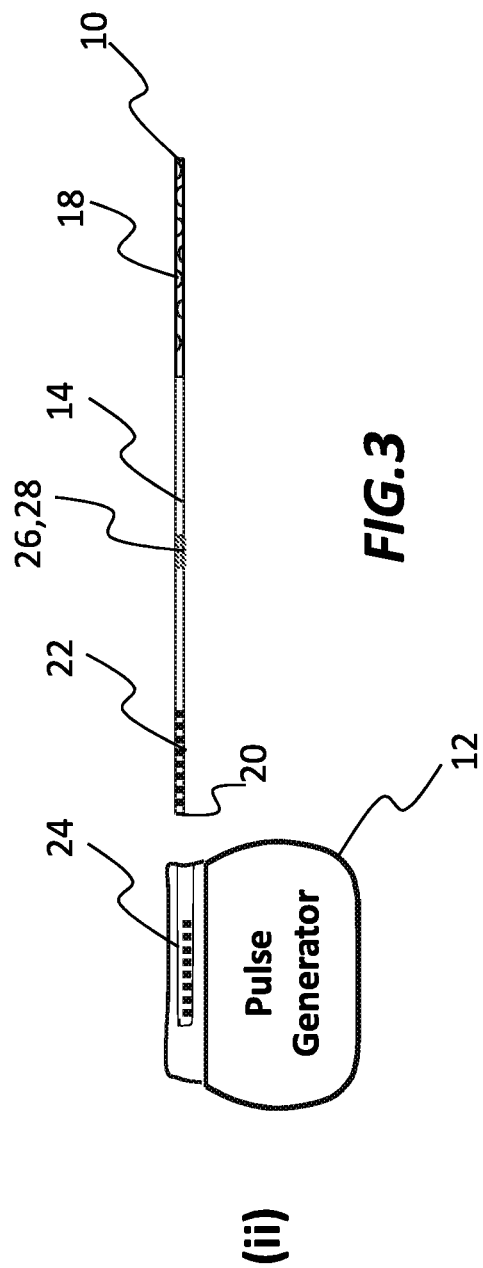
FIG. 3 schematically shows a pulse generator and a multi-contact, cylindrical electrode array containing a hermetic enclosure with active electronics that may be assembled, bonded, and configured for therapy delivery in accordance with illustrative embodiments of the invention.

As shown in FIG. 3, the IPG 12 may have more than one connector port 24 to facilitate the attachment of the lead 14. As with other embodiments, this embodiment of the multi-contact electrode array 10 contains ring contacts 22 on its port plug 20, and the lead body 14. Stimulation contacts 18 are disposed around the tip of a cylindrical surface to spatially deliver therapy, for placement using a needle or catheter. The lead 14 also contains the hermetic sealed enclosure 26 containing an electronic device 26/28 (e.g., a multiplexer).

Implantable neurostimulators, including both "open-loop" (no physiological feedback) and "closed-loop" (with physiological feedback) paradigms, provide a means to deliver electrical stimulation to provide optimal scheduling or delivery of therapy. Optimal delivery may incorporate closed-loop approaches of measuring a sensed state or parameter, such as a physiological functions (e.g., respiration, electrocardiogram, gait, or muscle response) and stimulating neural tissue such as the spinal cord, brain, retina, cochlea, and autonomic nerves in response to a sensed state. Closed-loop recording from peripheral nerves, the spinal cord, cortical tissues, or other physiological functions provides feedback information that can be used to inform enhance stimulation therapy in a closed-loop fashion.

Conventional implantable neuromodulation pulse generators (e.g., spinal cord, deep brain, and bladder stimulators) deliver therapy typically using 4, 16, or 32 electrode contacts, but are limited by a one-to-one wiring requirement in the lead body: each additional stimulation site requires an additional lead body conductor, electrode contact, and voltage/current source circuit. This one-to-one requirement presents a significant obstacle to scalability to 32, 64, or more electrodes due to wire stiffness, surgical workflow of managing wires and connectors, device size, and manufacturing cost.

The number of conductors and contacts in a pulse generator header and lead body may be reduced (including a smaller overall implanted device) if an electronic device can be positioned nearer to the tissue being stimulated. A wireless miniaturized device could be positioned adjacent to the nerve or spinal cord. Additionally, a current source, multiplexer, or other circuit could be positioned along a stimulation lead closer to the therapy target resulting in a greater number of output electrode contacts but with fewer wires connecting the lead to the pulse generator.

Similarly, implantable devices typically need to be MRI (magnetic resonance imaging) compatible to enable patients implanted with the device to be eligible for subsequent MRI scanning. This may be important for patients with thoracic spinal cord stimulators. Conventional electrodes are known to cause heating at the electrode sites due to 64 and 128 MHz electric fields localizing near the electrode array sites. Positioning active circuitry between the pulse generator and the electrode therapy contacts provides a disconnection approach, preventing the MRI signals from reaching the therapy electrodes. The electronic component may exist along the length of the lead body, or at a beneficial distance to divide the length of the lead with respect to the wavelength of the MRI resonance. Conventional methods have included high-impedance circuit components (e.g., inductances) at the distal ends of leads to increase the impedances to serve as a reflection coefficient to the RF wave induced on the lead. Active circuitry along the lead body can serve as an open circuit, short circuit, or impedance discontinuity to alter the electrical length of the lead to reduce coupling efficiency of MRI signals into the tissue through the electrode sites. Additionally, an active circuit containing an electronic switch at the end of a lead may result in the lead being completely disconnected at RF frequencies from the therapy contacts creating a unique approach to MRI heating.

In various embodiments of the invention, the implantable hermetic enclosure 26, which contains the electronic device 28, is permanently (e.g., welded) bonded to the flexible multi-contact electrode array 10 containing continuously conducting elements. The implantable hermetic enclosure 26 may have a variety of shapes, sizes, and geometries for attachment of the flexible, multi-contact electrode array 10.

Figure 4:
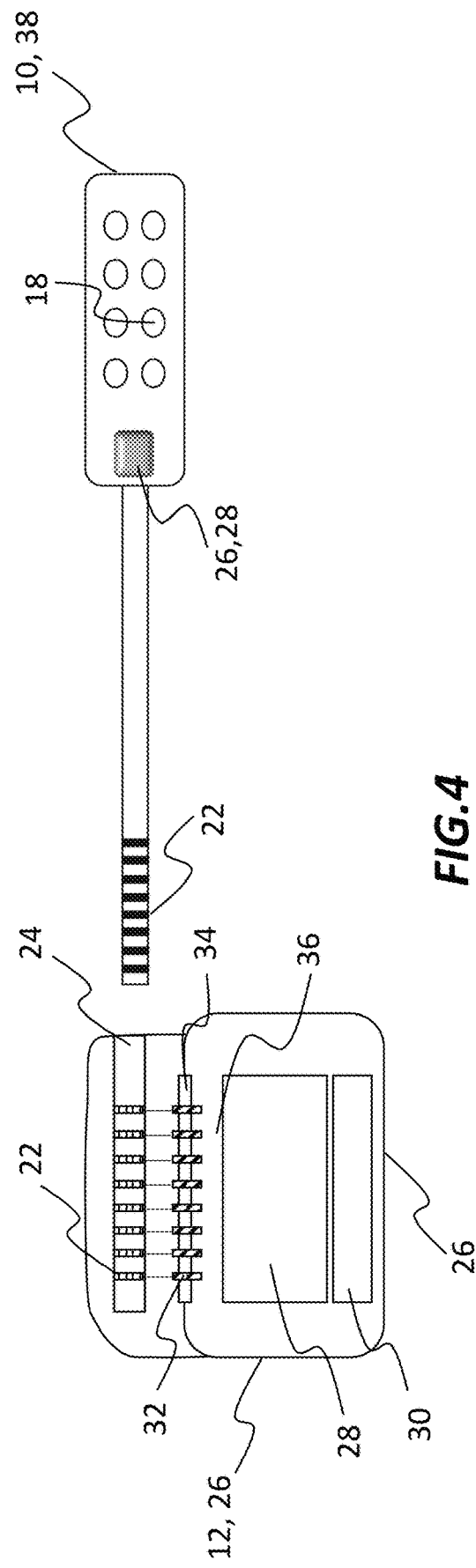
FIG. 4 schematically shows a pulse generator having a hermetically sealed enclosure and a hermetic feedthrough array on the circumferential edge of the enclosure. The hermetic feedthrough array electrically couples internal electronic devices to contacts on the header port plug. The active lead contains a hermetic enclosure with active electronics and a flexible, multi-contact electrode array that may be assembled, bonded, and configured for therapy delivery in accordance with illustrative embodiments of the invention.

FIG. 4 schematically shows more details of the implantable hermetic enclosure 26, which preferably provides a hermetic, gas-tight and water-tight barrier for electronic devices 28, energy sources 30, PCB circuitry 28, and mechanical components. A typical enclosure hermeticity test has a helium desorption leak rate of $1\times10^{-9}$ atm-cc/sec according to MILSTD 833: 1014. Other finer leak testing can be performed to $1\times10^{-10}$ using cumulative helium desorption testing. To that end, the enclosure 26 may be produced from a mechanically robust hermetic material (e.g., titanium, ceramic, zirconia, diamond, glass, etc.). In addition, the enclosure may contain an inert gas, or it may be completely filled with an insulating material free from voids.

FIG. 4 shows electrical connections on the IPG 12 made from the internal electronic device 28 to the exterior of the hermetic enclosure 26 using hermetic feedthrough conductors 32. A hermetic feedthrough 32 or hermetic feedthrough array 32 includes an insulating substrate 34 formed from an inert material (e.g., ceramic, alumina, glass, zirconia, diamond, etc.) with conductive feedthrough conductors (e.g., feedthrough pins 32) formed from a conductive, biocompatible, and noble metal (e.g., tungsten, titanium, platinum, platinum-iridium, stainless steel, platinum powder, composite materials, or multi-piece integrated materials). Alternative embodiments of the substrate 34 may be made of a metal with only insulating dielectrics around each feedthrough conductor 32.

Hermetic feedthrough conductive elements 32 may be produced using wire or pins forming a discrete conductive element, and then hermetically bonded using brazing, pressing, or laser-welding. Other composite feedthrough embodiments may form the feedthrough conductors 32 with screen printing or depositing conductors into vias (e.g., HTCC, LTCC). In another multi-piece feedthrough embodiment of the invention, two or more conductive materials may be bonded together, such as formed conductive via joined to a discrete conductor (e.g., deposited, screen printed, or conductive power), two solid material conductors (e.g., concentric shapes), or two composite materials.

Hybrid integrated methods may utilize filled conductive vias joined with a discrete conductive solid element using a joining or coupling method (e.g., brazing, sintering, firing, mechanical bonding, etc.). One or more feedthrough conductors 32 may be disposed in a single insulating substrate 34. Feedthrough conductors 32 may also contain discrete insulators and rings for positioning in a conductive, non-insulative substrate (e.g., titanium).

In some embodiments of the invention, the hermetic feedthrough conductors 32 may have diameters of approximately 50 um (micrometers)-2000 um, and the spacing between the feedthrough conductors 32 may have a 100 um to 2500 um center-to-center distance. Some methods could be used for larger feedthrough diameters and spacings, but miniaturization and volume demands typically require smaller and more tightly packed feedthrough conductors 32.

Referring again to FIG. 4, hermetic feedthrough conductors 32 may be positioned on the perimeter edge of a device. An internal connection 36 to electronic circuitry in the hermetic feedthrough conductors 32 may be performed using soldering to a rigid-on-flex circuit board or other methods. An external connection to the feedthrough conductors 32 may be performed using a wire or pre-formed metallic element permanently connected to ring contacts 22 of the port plug 24 using conventional welding approaches.

Figure 5:
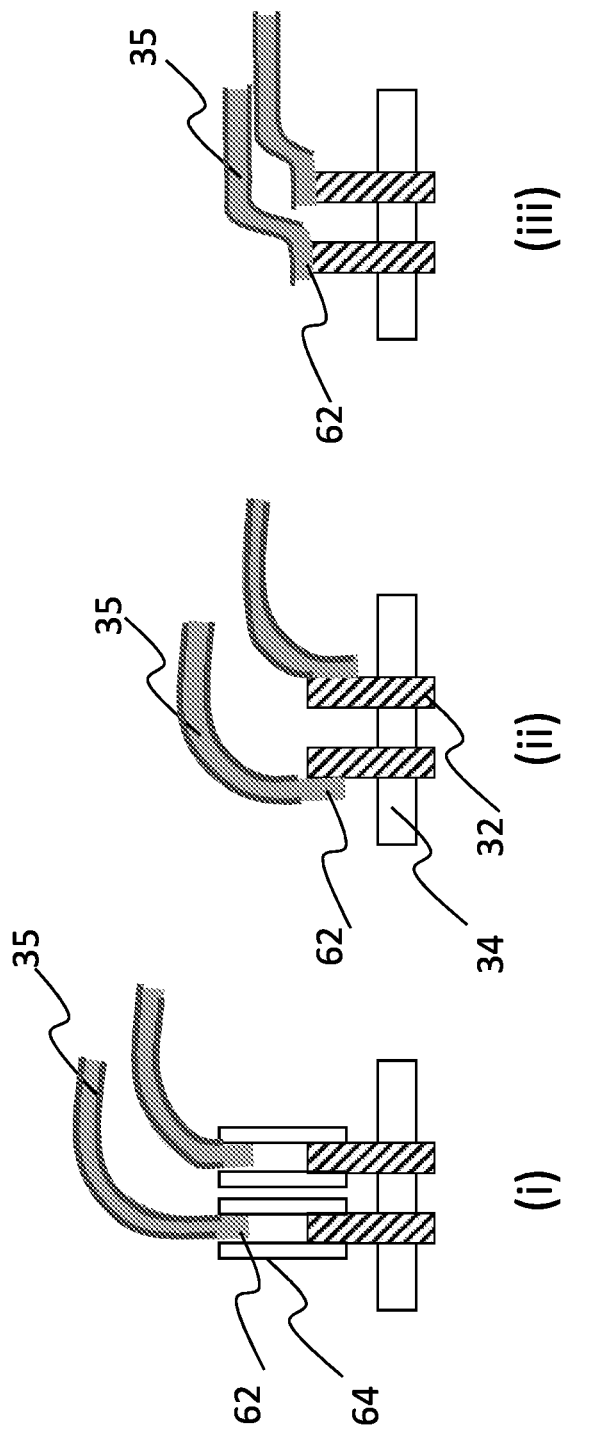
FIG. 5(i)-(iii) schematically shows prior art methods of attaching discrete, de-insulated wires to hermetic feedthrough conductors on the outside of the hermetic enclosure.

FIG. 5 shows prior art electrical connections to hermetic feedthrough conductors 32 on the external side of a hermetic enclosure. In this case, the connections have been performed by connecting wire or folded discrete metal components followed by an encapsulation. In FIG. 5(*i*), an insulated wire 35 has a de-insulated section 62 placed into a crimp or welding tube 64, which is positioned over the feedthrough 32. In FIG. 5(*ii*), the de-insulated portion of the wire is bonded to the circumferential surface of the feedthrough pin using a bonding process such as welding. In FIG. 5(*iii*), the de-insulated wire is directly bonded to the face of the hermetic feedthrough. In a similar fashion, discrete metal rods, folded metal, pins, ribbons may be bonded between hermetic feedthrough conductors 32 and ring contacts on the header and encapsulated in an epoxy or insulating material. Each of these techniques suffers from robustness and reliability problems.

Electrodes

In various embodiments, the flexible, multi-contact electrode array 10 is embedded with at least one layer of continuously conducting elements 42 bonded to the hermetic feedthrough array 32. Those elements 42 may take a variety of forms, including as traces integrated into their underlying substrate. In preferred embodiments, the continuously conducting elements connecting a contact/pad/electrode to another contact/pad/electrode are formed by laser-processing a thin layer of conductive material (e.g., a conductive foil). In other embodiments, the conductive element could be applied through a deposition process (e.g., deposition, electrodeposition, printed). The conductive material preferably extends from one point to another point and serves as a continuous electrical conductor to electrically connect the two points (e.g., an electrode in the array 10 with another electrode). Thus, the continuous conductive elements are not expected to have breaks that would interfere with conduction between the ends.

Moreover, some embodiments form the continuous conductive elements 42 as a plurality of discrete but coupled conductors in electrical contact (e.g. two elongated traces in abutting, electrical contact). Other embodiments may form the continuous conductive elements as integral components, and in some instances, integral with pads 44 and 48 at either end (e.g., integral with a pad 44 in the array 10 and pads 44, discussed below). In this latter case, the continuous conductive element, while separate from the pads 44 and 48, may form a single, unitary component on its underlying substrate. Some such embodiments may deposit the continuous conductive elements and the electrodes at both ends in a single deposition step (e.g., a printed conductor).

Moreover, as noted above, the continuous conductive elements preferably have a thin, ultra-low profile, such as between about 5 and 200 microns. For example, the thickness of the continuous conductive elements (i.e., the material dimension in a direction perpendicular to the substrate supporting them) may be between about 5 and 190 microns, between 18 and 100 microns (e.g., between 18 and 52 microns), and between 15 and 50 microns (e.g., between 12 and 18 microns). For applications requiring visibility of the conductive elements under radiographic imaging (e.g., fluoroscopy), the thickness of the continuously conductive elements may have a thickness greater than 50 microns. Some embodiments have generally consistent thickness continuous conductive elements, within reasonable tolerances, while other embodiments may form the continuous conductive elements with more than one different thickness (i.e., its thickness may vary).

The continuous conductive elements may be formed from a conductor material, such as a substantially flat, thin continuous metal conductor layer (e.g., a metal film or metal foil) or other weldable material, with insulating elastomer material 34 encapsulating the continuous conductive elements on all sides, or other conductive material (preferably a weldable material). For additional robustness, the continuous conductive elements may contain anchor features, such as slits, hooks, or holes, enabling insulating elastomer layers 34 to anchor the continuous conductive elements to the elastomer.

Other embodiments, however, may form the continuous conductive elements from a conductive polymer, electrodeposited material, or a hybrid of bulk material with deposited material. Several examples of hybrid materials may include a polymer having internal metal, conductive ink, conductive epoxy, or other conductive materials.

FIG. 6(*i*) shows a top view of the flexible, multi-contact array 10 with many electrode sites 44 ("therapy contacts") exposed to the tissue, efficiently providing multiple points of electrical connection with the spinal cord or other tissue. In illustrative embodiments, the electrode sites 44 form an array of pads/contacts 44. For example, the array may include no fewer than 16 or no fewer than 64 electrodes but no more than 128 electrodes. Other embodiments may have differing numbers of electrodes (e.g., between 4 and 512, or some other number). Electrical stimulation is applied through therapy electrode sites/electrode sites 44 to neural tissue (e.g., to spinal cord 16, dorsal roots, dorsal rootlets, peripheral nerves, dorsal root ganglia, subthalamic nucleus, other brain tissue, or other neural tissue) or other biological tissue (e.g., cardiac, muscle, etc.). Specifically, multi-contact arrays 10 improve therapy by selectively stimulating partial or sub-volumes of the neural tissue—by distributing stimulation energy (via cathodes and anodes) across one or more electrode sites 44 in proximity with the neural structure. In one embodiment, the multi-contact electrode array 10 enables therapy to be precisely delivered to a sub-volume of the neural target (e.g., specific columns of the spinal dorsal column, particular dorsal root entry zone, dorsal root ganglia, one or more fascicles within a peripheral nerve, ganglia, etc.). It should be noted that although the arrays 44 are depicted as curved, they also may be rolled into a cuff electrode, for example, flat, or irregularly shaped.

Prior-art conventional implantable multi-contact electrode arrays known to the inventors are assembled by linking non-continuous conductive elements (discrete metal contacts, discrete wires, etc.). After the multiple conductive elements are connected (e.g., using welding, swaging, or crimping) and placed in a fixture, injection molding techniques position the conductive elements within an insulating elastomer. Such conventional approaches, however, undesirably do not scale well to ultra-thin (i.e., less than 1 mm), low-profile geometries or to high-channel count electrodes (e.g., 16, 32, 64, or 128 electrodes). In particular, conventional injection molded electrodes assemblies are inherently thick (e.g., about 2 mm) due to the bulk volume required for the combination of components and to facilitate the flow of encapsulation during the assembly process. Assembling non-continuous conductive elements and their density limitations of positioning and welding individual contacts and wires also limits these approaches from efficiently scaling to more than 16 or 32 electrical contacts.

Prior-art miniaturized implantable devices (e.g., retinal stimulators) with more than 32 electrode contacts have utilized semiconductor micro-fabrication methods to produce flexible electrodes based upon insulator and conductor deposition methods (evaporation, sputtering, vapor deposition, requiring etching, liftoff, etc.) to create ultra-thin conductive elements (e.g., less than 2 microns) comprising electrode arrays of electrode arrays of 32, 64, 128 on ultra-thin substrates (e.g., less than about 20 microns). In commercially reasonable applications, however, such semiconductor depositions methods cannot reasonably be increased above 5 micrometer of conductor thickness, as thicker depositions have inherent stress limitations that result in conductor cracking or detachment from the substrate. Thin-film conductors are inherently not thermally weldable due to the thickness and mechanical properties.

As shown in FIG. 6, which shows the flexible multi-contact electrode array 10 of illustrative embodiments as containing a biocompatible insulating substrate material 45 (e.g., silicone, elastomer, co-polymer, urethane, liquid crystal polymer, etc.) that has at least one layer of continuously conductive elements 42. The electrode substrate 45 is flexible in three-dimensions and, in one embodiment, is preferentially comprised of a soft elastomer, such as silicone, with a low modulus and rigidity that reduces the risk of tissue damage. The Young's modulus of silicone is closer to neural and soft biological tissue than many micro-fabricated thin-film materials (e.g., deposited or spin-on polyimide or parylene, etc.) with a flexural rigidity is 1-2 orders of magnitude softer. The insulating substrate may also be made of other materials such as polyurethane, liquid crystal polymer (LCP), silicone-urethane co-polymer, or polyethylene terephthalate (PET). In illustrative embodiments, the substrate 45 has a Youngs Modulus of between about 1 megapascal and 5 gigapascals.

As known by those skilled in the art, each electrode site 44 has a conductive surface for delivering electrical stimulation to body tissue. The continuous conductive elements 42, within the insulating substrate 45, transmit electrical current from the connection pads 48 to the electrode sites 44. Insulating substrate material between the continuous conductive elements 42, connection pads 48, and the surrounding body tissue prevents short circuits and ensures that unintended electrical current does not leak into or otherwise interact in an unintended manner with the body tissue or other continuously conducting elements. To improve robustness for normal implanted use, the continuous conductive elements 42 may be configured in a serpentine pattern to form strain relief features, enabling the continuous conductive elements 42 to flex when subjected to certain expected forces within a patient's body (e.g., a longitudinal force exerted on the electrode array 10).

FIG. 6 shows a reinforcing material 56 that may be embedded within one or more areas of the insulating substrate 45 to mechanically strengthen the electrode array substrate assembly without increasing rigidity or appreciable thickness. During repetitive strain, the reinforcement material 56 absorbs the mechanical forces to mitigate the risk of breaking the conductive portions of the electrode. Among other things, this reinforcing material 56 includes open areas, pores, strips, or apertures to allow the insulating material to continuously encapsulate the reinforcing material (e.g., micro-fiber, woven mesh, honeycomb, or carbon fiber).

The flexible, multi-contact electrode array 10 preferably is bonded to the hermetic feedthrough array 32. The continuously conducting elements 42, as well as the electrode sites 44 and connection pads 48, preferably are formed from a thin, continuous conductor material, such as a metal conductor layer or foil of noble metal (e.g., platinum-iridium, stainless steel, platinum, palladium, etc.) with insulating elastomer material 45 surrounding the continuous conductive elements. To further increase the number of electrode sites 44 and their density, the substrate 45 also may include more than one layer of continuous conductive elements 42 separated by an insulating material. For example, the substrate 45 may have two continuous conductive element layers and three elastomer layers, increasing the contact density. The continuous conducting elements 42 and feedthrough conductors 32 provide mechanically advantageous properties for welding to hermetic feedthrough conductors 32 of the hermetic enclosure 26.

Referring to FIG. 6(ii), the multi-contact electrode array 10 is flexible and conformal in shape due to its advantageous substrate material properties. It may also be conformal over a 3D surface.

Welding

Prior art micro-fabricated thin-film and flexible circuit electrode arrays known to the inventors generally are delicately bonded to hermetic feedthrough arrays using a variety of additive-material methods. The need for an additive material stems from (a) the insufficient volume of ultra-thin deposited conductive materials (e.g., less than about 5 microns) required to form a bond without creating a void or hole resulting in bond failure, and (b) the addition of softer materials (e.g., gold bumps) to form an intermetallic bridging layer between the feedthrough and electrode material. Methods for bonding these fragile conductors have included additive material processes such as wire-bonding, wedge bonding, rivet bonding, solder bonding, electrodeposition methods, electroplating, conductive polymers, staple-wire welding, anisotropic conductive materials, and combinations thereof.

These additive approaches often used in semiconductors are difficult to use with implantable medical device applications for at least two reasons:

(1) conductive materials commonly used for semi-conductors (e.g., copper, nickel, gold) may not be biocompatible or may have bulk metal migration when carrying current in saline, and (2) bonding of noble metals, such as platinum, is difficult without additive layers or lower-temperature intermetallic materials (e.g., nickel, gold).

Such additive approaches also have significant fragility, poor mechanical yield, and are costly to manufacture. Delicate deposited conductors have highly resistive conductor properties that are unsuitable for therapies requiring higher-current (e.g., SCS requires 1-25 milliamps of stimulation whereas retinal implants normally require 100 microamps to 8 milliamps). Similarly, delicate and low-current carrying bonds and conductors do not provide safety against defibrillation.

Figure 7:
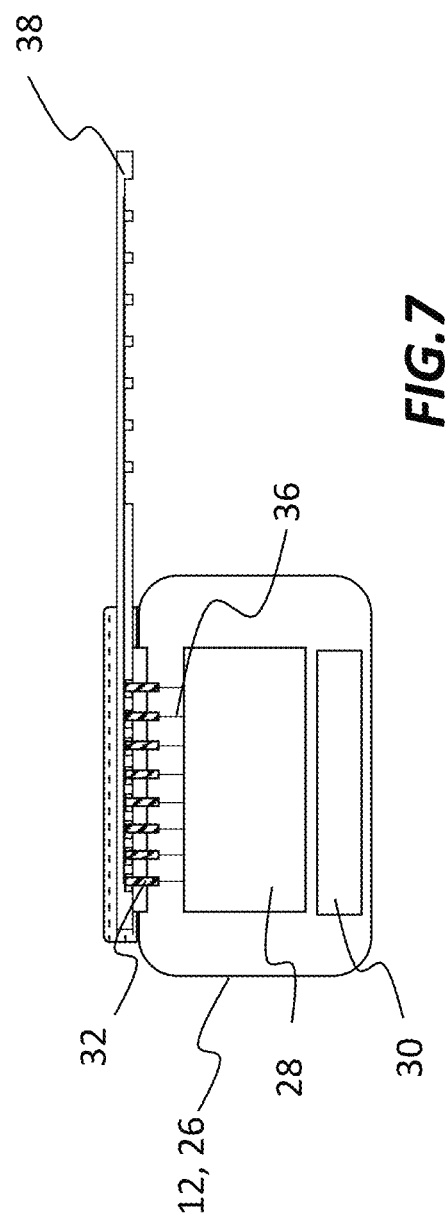
FIG. 7 schematically shows a signal generator (e.g., a pulse generator) having a hermetically sealed enclosure and a hermetic feedthrough array on the side of the enclosure. The hermetic feedthrough array electrically couples internal electronics to stimulation contacts on a flexible multi-contact electrode array that may be assembled, permanently bonded, and configured for therapy delivery in accordance with illustrative embodiments of the invention.

FIG. 7 shows one embodiment that employs a flexible, multi-contact electrode array 38 embedded with continuously conducting elements 42 bonded to a hermetic enclosure 26 containing feedthrough conductors 32. In this example, the feedthrough conductors 32 are positioned on the circumferential edge of the hermetic enclosure 26 of the IPG 12 containing PCB circuitry 28 and an energy source 30. Permanent bonds, preferably welded bonds, are formed between the faces of the hermetic feedthrough conductors 32 and the connection pads 48 of the flexible, multi-contact electrode array 38.

Figure 8:
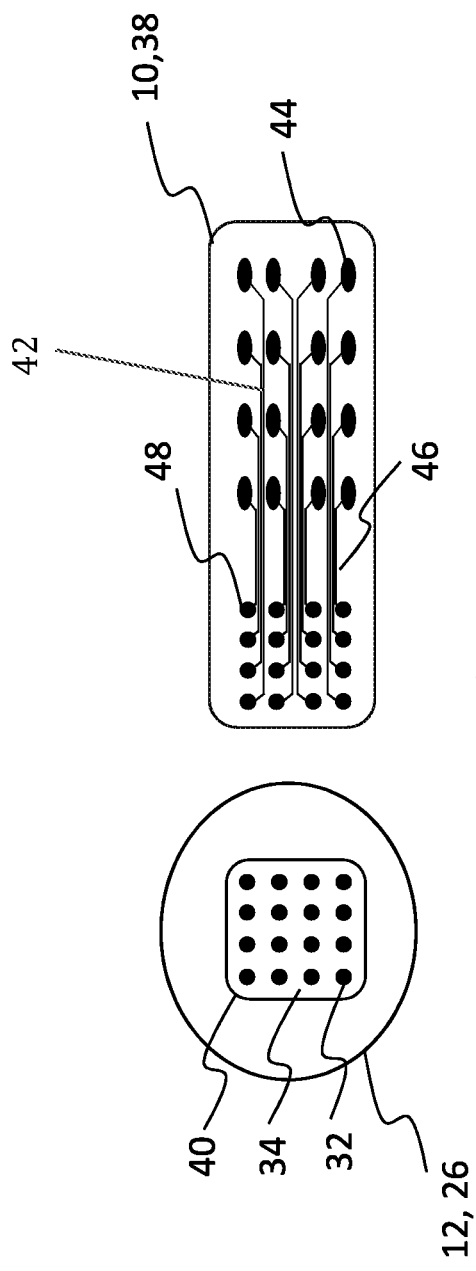
FIG. 8 schematically shows a top view of an implantable device having a circular hermetic enclosure with a hermetic feedthrough array positioned on the face of the enclosure and a flexible active electrode array that may be assembled, permanently bonded (e.g., welded), and configured for therapy delivery in accordance with illustrative embodiments of the invention.
Figure 9:
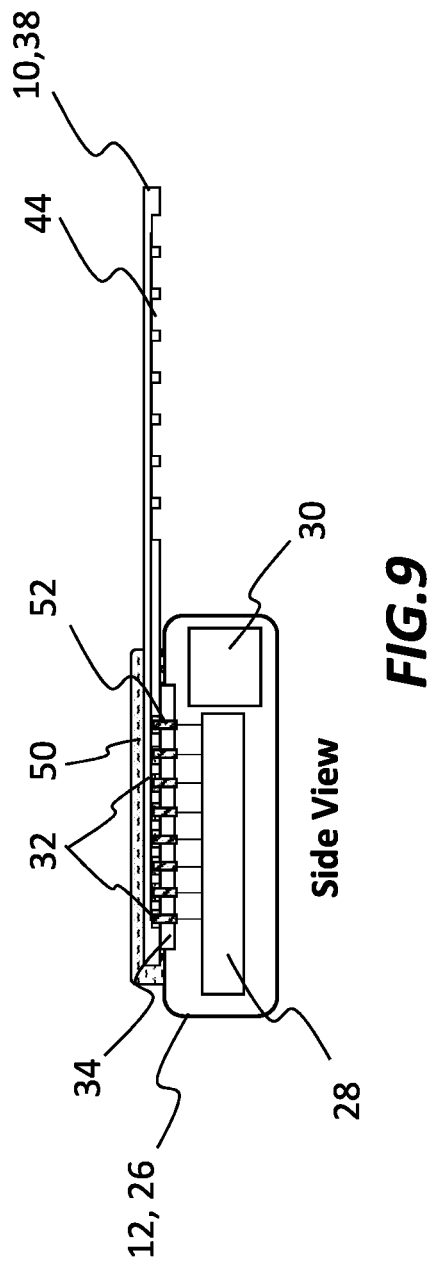
FIG. 9 schematically shows the cross-sectional view an implantable device having a circular hermetic enclosure with a hermetic feedthrough array positioned on the face of the enclosure and a flexible active electrode array assembled, permanently bonded (e.g., welded), and configured in accordance with illustrative embodiments of the invention.

Referring to FIGS. 8 and 9, a flexible, multi-contact electrode array 38 embedded with continuously conducting elements 42 with connection pads 48 and electrode sites 44 is positioned next to a circular hermetic enclosure 26 on the face of the enclosure 26. The feedthrough array 32 includes hermetic feedthrough conductors 32, the hermetic insulating substrate 34, and a hermetic ring 40.

FIG. 9 depicts the side view of the multi-contact electrode array connection pads 48 after permanent bonding (preferably welded bonds) to the hermetic feedthrough conductors 32, with permanent bond sites. A layer of adhesive or encapsulating material 50 is applied to insulate the adjacent feedthroughs and bond. The electrodes are depicted on the same side of the electrode array 38 as the hermetic package but may also be on the opposite side. As noted above, the connection pads 48 are welded to the feedthrough conductors 32, which, as known by those in the art, involves a portion of the connection pad and a portion of the feedthrough face becoming temporarily liquified, which then solidify to form a spot weld or nugget. In this embodiment, for a given pad 48 and feedthrough conductor 32, the material of the given pad 48 and feedthrough conductor 32 combine in a conventional manner to form a mechanical coupling.

Figure 10:
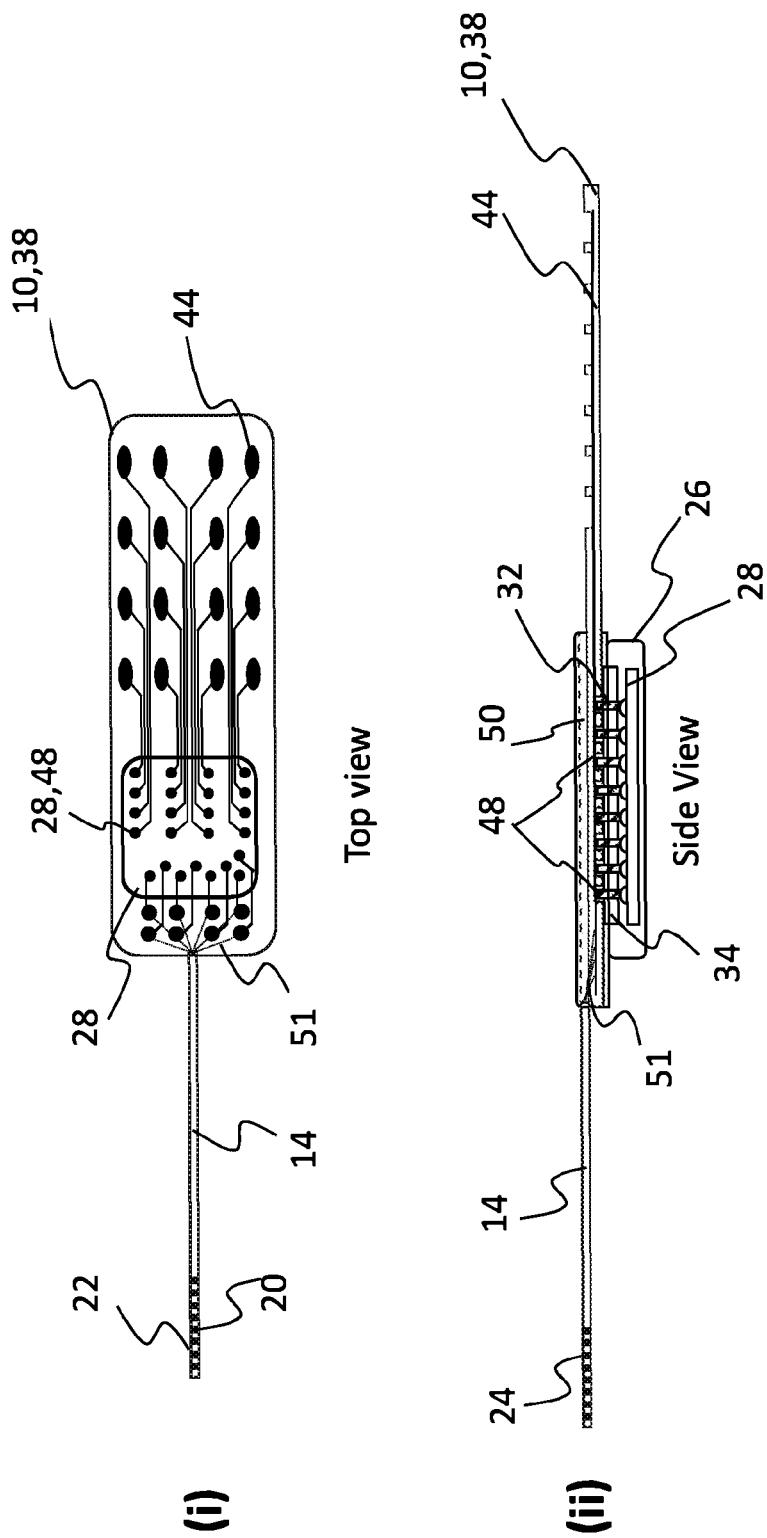
FIG. 10 schematically shows respective top (i) and side (ii) views of a flexible, multi-contact active lead in illustrative embodiments with a proximal lead body for connection to a header port or lead extension, an electronic device in a hermetic enclosure, and a flexible therapy array.

FIG. 10 schematically shows the top view (i) of an assembly of an active electrode array 38 containing the connector plug 20, the lead body 14 with conductors 51, the hermetic enclosure 26 containing the electronic device 28, and the flexible, multi-contact electrode array 38. It is noteworthy for an active-lead 14 containing an electronic device that the number of ring contacts 22 is generally fewer than the number of electrode sites 44 due to the electronic device 28 function.

FIG. 10(ii) shows a cross-section of the assembly showing the implantable hermetically sealed enclosure 26 bonded to the flexible, multi-contact electrode array 38 and lead body 14. The permanent bonds (preferably welded) between the connection pads 48 to the hermetic feedthrough conductors 32 are depicted. The electronic device 28 preferably is flip-chip bonded to the internal faces of the hermetic feedthrough conductors 32. The tissue contacting electrodes are depicted on the opposite side as the hermetic package, but may also be positioned on the same side.

Figures 11, 12, 13:
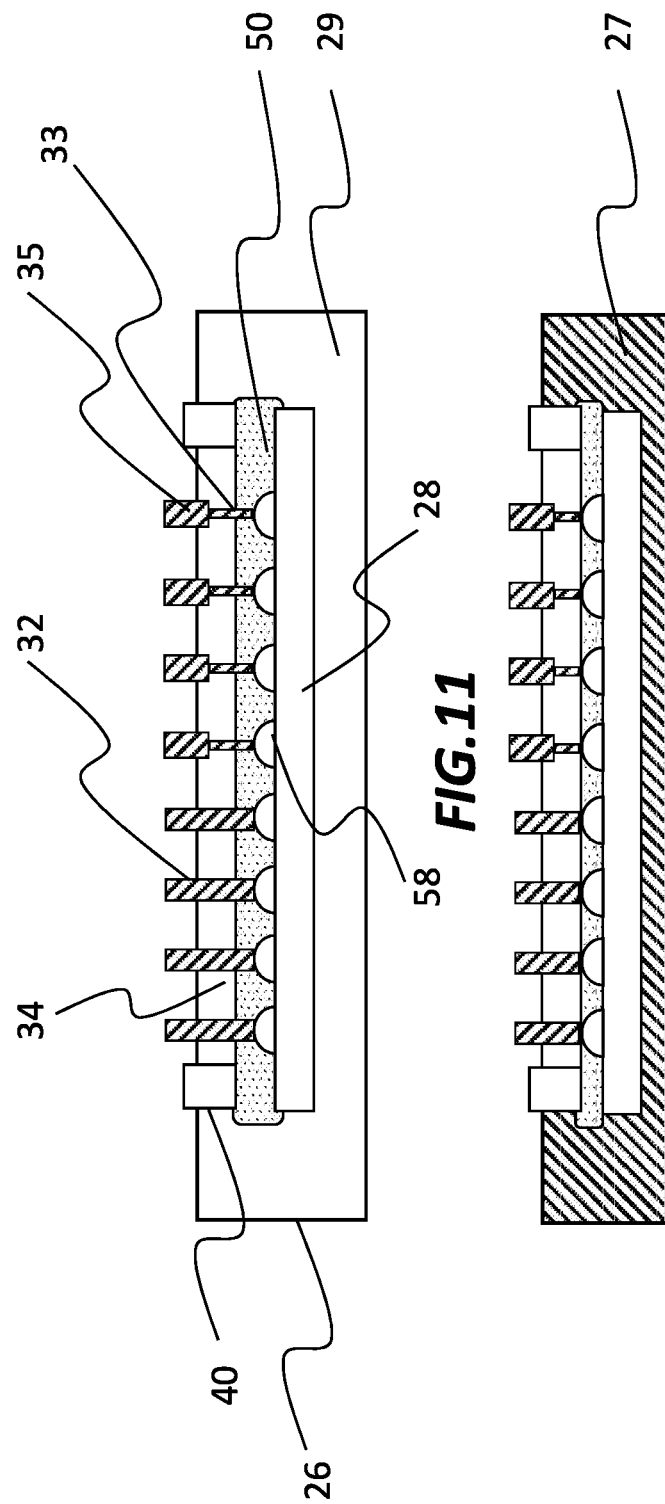
FIG. 11 schematically shows the cross-sectional view of an electronic device bonded inside a gas-filled (hollow) hermetically sealed enclosure with hermetic feedthrough in accordance with illustrative embodiments.
FIG. 12 schematically shows the cross section of an electronic device bonded inside a void-free (encapsulated/filled) hermetically sealed enclosure with hermetic feedthrough conductors in illustrative embodiments.
FIG. 13 schematically shows various configurations and geometries of hermetic feedthrough conductors and various offset positions of the external and internal feedthrough faces with respect to the hermetic insulating substrate in illustrative embodiments. Multiple types of single-piece (i)-(iii) or hybrid multi-piece (iv)-(vii) conductive feedthrough conductors are shown.

FIG. 11 shows a cross-sectional view of an embodiment of a package 29 having the implantable, hermetically sealed enclosure 26 with a hermetic ring 40, hermetic insulating substrate 34, solid hermetic feedthrough conductors 32, and a plurality of via-type hermetic feedthrough conductors 32 that each has a bulk conductive post 35. One or more electronic devices 28 may be bonded internally to hermetic feedthrough conductors 32 using a bonding method. In one embodiment, the internal bond between the feedthrough conductors 32 and electronic device 28 uses solder balls 58. The area between the electronic die and/or component 28 and the insulating substrate may be underfilled with an insulating adhesive, underfill epoxy, or encapsulant. Although not depicted, traces may be patterned to the interior of the ceramic package 29 using deposition, sputtering, screening, or other processes that may also facilitate other electronic components. Also, the interior of the package 29 may contain a moisture getter (not depicted), such as an anhydrous salt, which enlarges the effective volume of the internal enclosed volume. The hermetic system shown in FIG. 11 may contain an enclosed air volume normally filled with an inert gas such as helium, nitrogen, or argon.

FIG. 12 shows another embodiment in which the implantable enclosure does not have an enclosed air volume and is instead filled with an insulating material with low water absorption and diffusion properties. Among other things, the filler material may be an encapsulant, adhesive, elastomer, or other insulating material.

FIG. 13 depicts multiple hermetic feedthrough types and positions with respect to the hermetic insulating substrate 34. In: (i), a solid conductive feedthrough 32 protrudes from both the internal and external surface of the insulating substrate, (ii) the external protrusion is flush with the insulating substrate, and (iii) the feedthrough is flush on both internal and external sides. Similarly, a hybrid feedthrough comprised of a via 33 and a solid conductive post/pin 35 may also protrude or be flush with the internal or external surfaces of the insulating substrate as shown in (iv) to (vii). Though not shown, feedthrough conductors 32 may also be recessed from the surface.

Figure 14:
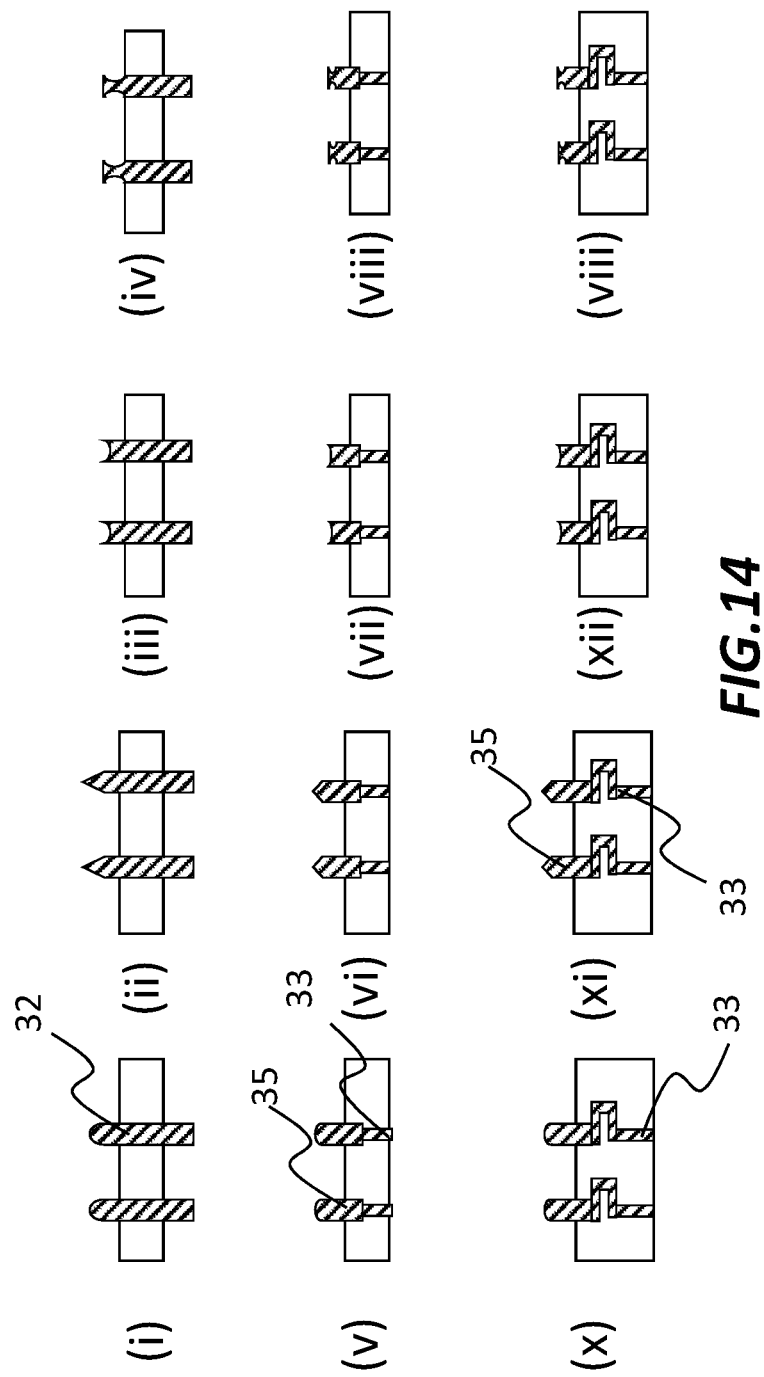
FIG. 14(i)-(iv) schematically show solid and seamless hermetic feedthrough conductor faces with rounded, pointed, convex, and concave external faces in illustrative embodiments.
FIG. 14(v)-(viii) schematically show hybrid multi-piece conductive feedthroughs (e.g., hermetic via brazed to a discrete solid metal post) with rounded, pointed, convex, and concave external faces in accordance with illustrative embodiments.
FIG. 14(x)-(xiii) schematically show a layered hybrid feedthrough approach (high temperature co-fired ceramic) providing conductive multi-part feedthroughs. A bulk piece with rounded, pointed, convex, and concave external faces is attached to a serpentine high temperature co-fired ceramic ("HTCC") feedthrough in illustrative embodiments.

FIG. 14 shows various embodiments of the bulk conductive hermetic feedthrough conductors 32 (top row) and hybrid feedthrough conductors 32 (bottom row), which in this embodiment may have flat internal or external surface profiles to enable preferential surfaces for performing a robust, biocompatible permanent bond. The surface profiles may be machined, polished, tumbled, laser treated, coined, pressed, etched, electro-discharge machining, cold forming, thermoforming, molding, etc. to create the desired profile. Mechanical processing (e.g., machining, grinding) of the profiles of the feedthroughs may be performed on the individual pins prior to assembly and firing. Alternatively, the pins may be position and fired into the assembly after which the mechanical processing (e.g., machining, grinding) may be performed to achieve the desired surface finish.

In FIG. 14, a solid feedthrough (i, ii, iii, iv) may have an external face with a (i) round, (ii) pointed, (iii) concave, (iv) convex, or (v) irregularly shaped geometry. Similarly, a hybrid feedthrough may also contain various external surface profiles as those depicted in (v) to (viii). The internal surface profile is depicted as flat but may also be preferentially configured to attach electronic devices or flexible circuits. In another embodiment of the hybrid feedthrough (x, xi, xii, xiii), the feedthroughs are formed through the insulating substrate using a high-temperature, co-fired ceramic process (generally by depositing a conductive power and sintering). In one embodiment, the HTCC feedthrough passes straight through the substrate. In other embodiments, the HTCC feedthrough serpentines through the ceramic layers. To form protruding faces 35, the HTCC feedthrough is fused with a discrete conductive post or machined part.

Figure 15:
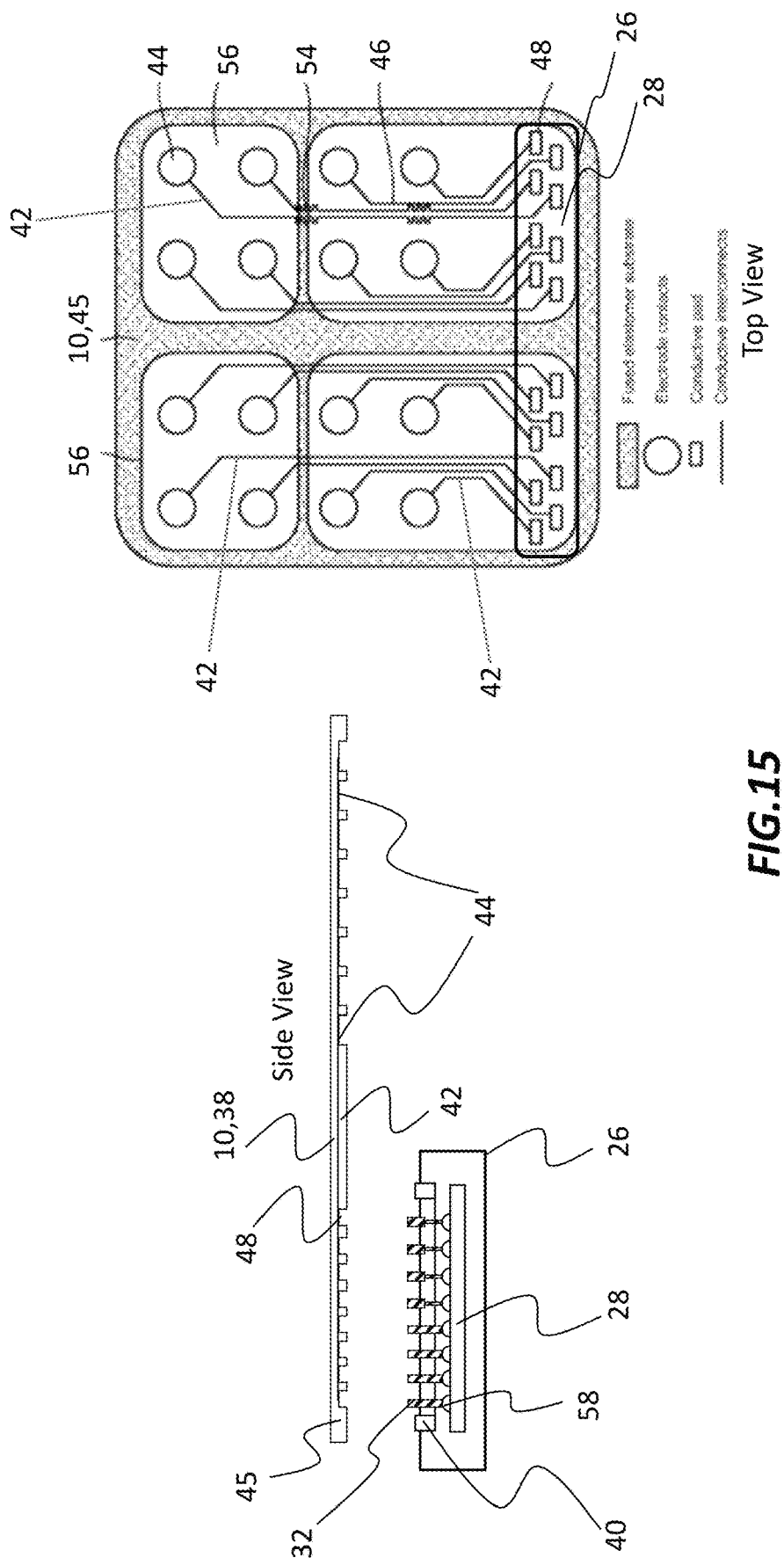
FIG. 15 schematically illustrates a flexible, multi-contact electrode array in accordance with illustrative embodiments of the invention.

FIG. 15 depicts a top view and a side view of a flexible multi-contact array 38 containing continuous conductive elements 42 and the hermetically sealed enclosure 26 prior to assembly. Connection pads 48 serve as the bond pad locations for joining to hermetic feedthrough conductors 32, such as through a weldable connection.

Figure 16:
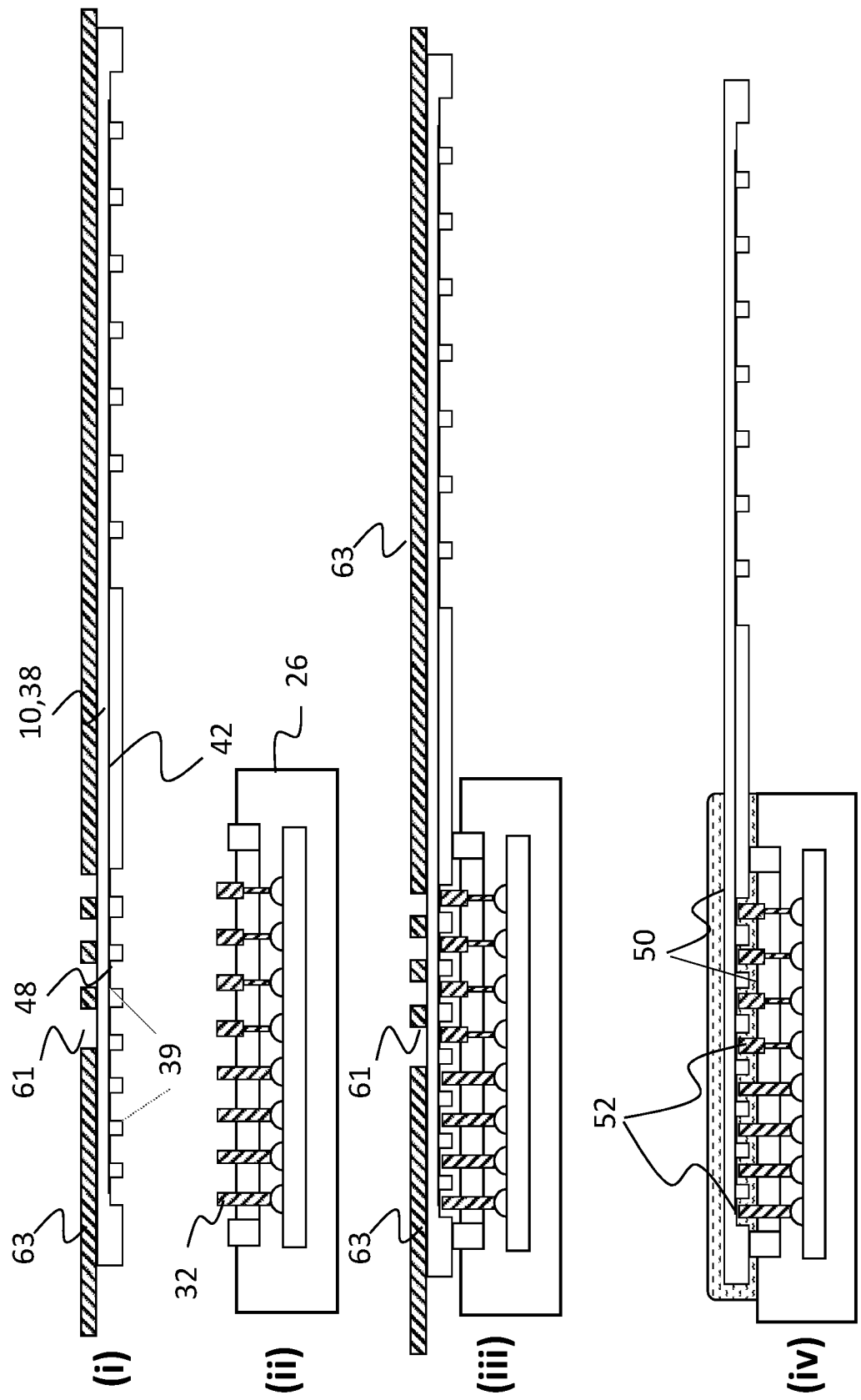
FIG. 16(i)-(iv) schematically show the process of assembling and aligning a flexible multi-contact electrode array and a hermetic enclosure containing an electronic device for permanent bonding in accordance with illustrative embodiments.

FIG. 16 schematically illustrates a process by which a biocompatible, insulated, and permanent bond is established between the flexible, multi-contact electrode array 38 with embedded continuous conducting elements 42 is shown in FIG. 16(i) and the hermetically sealed enclosure in FIG. 16(ii). The process begins when the sub-assemblies are brought into abutting contact as shown in FIG. 16(iii) (e.g., the feedthrough elements 32 are in abutting contact with the connection pads 48 on the array 38). An optional sacrificial carrier 63 with optimal rigidity properties may be used to (1) align the electrode array 38 to the feedthrough assemblies and (2) force abutting contact between the electrode and feedthrough assemblies. In one embodiment, the sacrificial carrier may have welding apertures 61 to enable multiple types of welding bonds. In some embodiments, the array 38 has a plurality of protrusions 39. When coupled with the hermetically sealed enclosure of FIG. 16(ii), each of the plurality of the protrusions is positioned between at least two adjacent feedthrough conductors 32. In another embodiments, the adjacent bond pads do not contain protrusions between them. Permanent electrical connection bonds are then formed using methods described herein. After welded conductor bonds are formed, an insulating material 50 preferably is used to underfill and overmold around the exposed continuous conducting elements 42 and hermetic feedthrough conductors 32. The insulating material encapsulates the permanently bonded joints as well as the conductive feedthrough and conductive elements providing a highly-isolated, water tight interconnections. The insulating material may be applied in one or more consecutive steps in a non-unitary body or unitary body fashion. As noted in co-pending U.S. patent application Ser. No. 15/806,005, the disclosure of which is incorporated herein, in its entirety, by reference, a unitary body may be seamless. For example, the unitary body may be formed as a unitary, fused body configured to mitigate weak bonding points.

Figure 17:
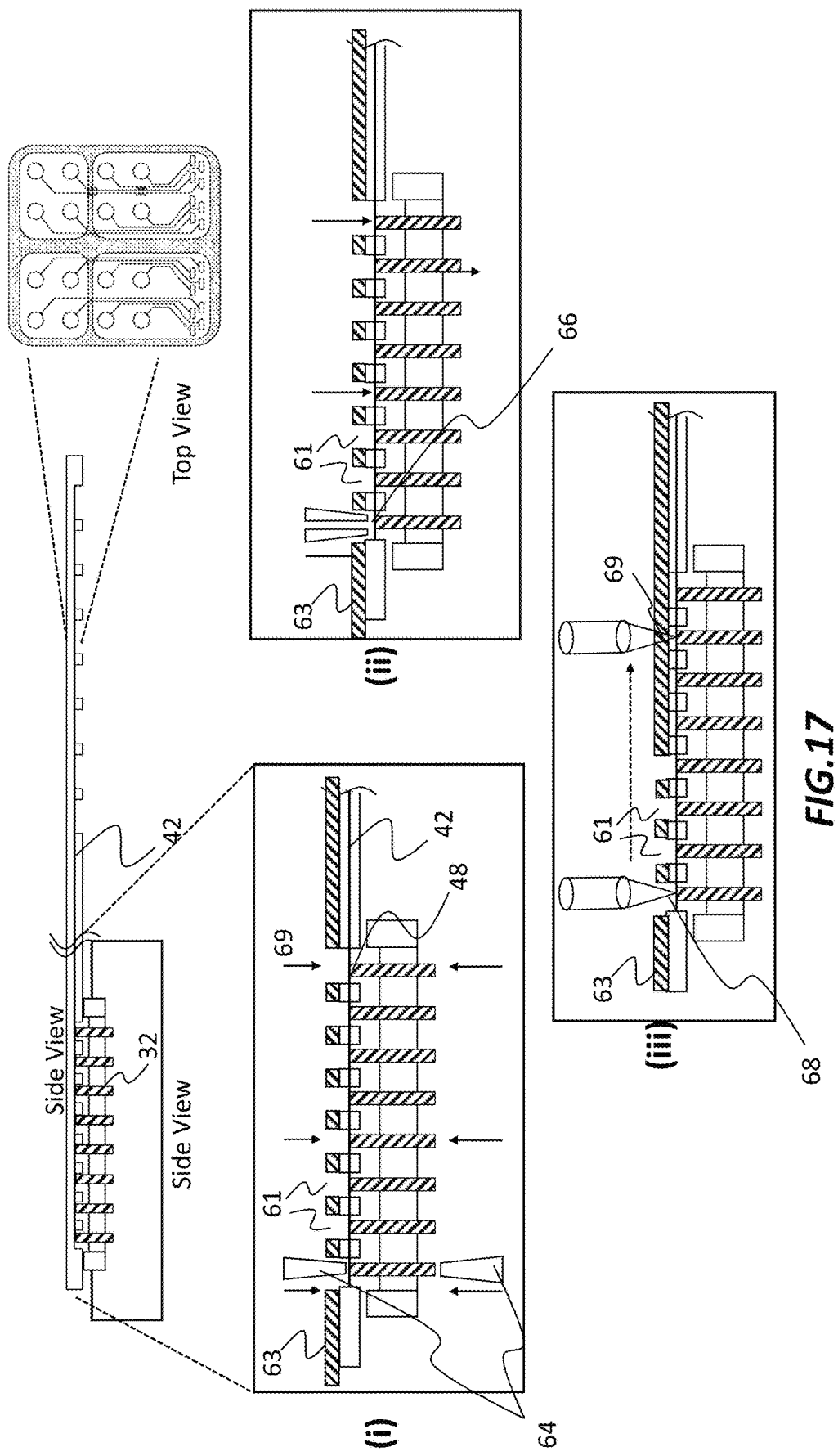
FIG. 17(i)-(iii) schematically shows the process of creating permanent bonds between the connection pads of continuous conducting elements and the hermetic feedthrough conductors using a plurality of thermal welding or joining processes in illustrative embodiments.

FIG. 17 schematically shows some processes of forming a permanent welding bond between the continuous conducting elements 42 and the conductive hermetic feedthrough conductors 32 in various embodiments. In FIG. 17(*i*), the conductive contact pad 48 of the continuous conductive element 42 is brought into close proximity or intimate contact with the face or surface profile of the hermetic feedthrough 32. In one optional embodiment, the process for bringing the electrode substrate and the connection pads into mechanical contact and alignment with the faces of the hermetic feedthrough assembly may be performed using a sacrificial carrier material 63. In another embodiment, no sacrificial carrier material is used. Due to the advantageous properties of the flexible, multi-contact electrode array 38 and the continuous conductive elements 42, non-additive methods of permanent bonding are preferential (e.g., welding). Referring to FIG. 17(*i*), opposed head resistance welding tips may be used from both sides to compress the contact pad 48 and weld to the feedthrough element 32. In FIG. 17(*i*), the welding tip is inserted through a sacrificial carrier 63 and carrier aperture 61 to enable the welding tip to contact the conductive connection pad. In another embodiment in FIG. 17(*ii*), a parallel-gap, spark-gap or thermocompression weld head forms a permanent bond from only one side of the hermetic feedthrough. In FIG. 17(*ii*), the welding tip is inserted through a sacrificial carrier 63 and carrier aperture 61 to enable the welding head to contact the conductive connection pad. In the embodiment of FIG. 17(*iii*), a laser welding beam is focused on the coupled connection pads and feedthrough faces and used to form a permanent welded bond between the elements. In one embodiment of FIG. 17(*iii*), the laser beam is focused through a sacrificial carrier material 63 containing apertures 61 enabling the laser-beam to pass unobstructed. In another embodiment, the laser beam is focused through a region 69 of the sacrificial carrier material which has optimal optical transmissive properties to enable the laser beam to form a weld of the underlying conductors.

Welding methods are preferable over additive methods, such as wire-bonding, which likely would have a lower bond strength. For example, a 25 micron wire bond may have a tensile strength of 1-5 gram-force, while a micron wire-bond may be approximately 10-20 gram-force. The permanent bond method of various embodiments is believed to be superior to these thin-film, such as wire-bonding, which have a bond break strength of less than 20 gram-force. For example, the use of a continuously conductive element with a thickness of 18 microns may provide a bond strength of 100 to 200 gram-force and a break strength of 100 to 500 gram-force, whereas a conductive element with a thickness of 36 microns may provide a bond strength of 200 to 800 gram-force and a break strength of 200 to 1000 gram-force. Preferred embodiments of bonding do not require additive materials (e.g., ribbons, wires, filler, etc.) and are thus non-additive techniques, such as welding (FIGS. 17(*i*), (*ii*), and (*iii*)). However, additive bonding methods may also be used to optimize the strength of the permanent bond—they can add another material to the connection of the pad 48 and feedthrough element 32. For example, coatings using a conductive material with a lower-melting point (e.g., gold) may be applied to the connection pads 48 or the feedthrough surface profiles or both to facilitate greater bond strength (e.g., metal alloy), bonding profile, or long-term reliability.

Figure 18:
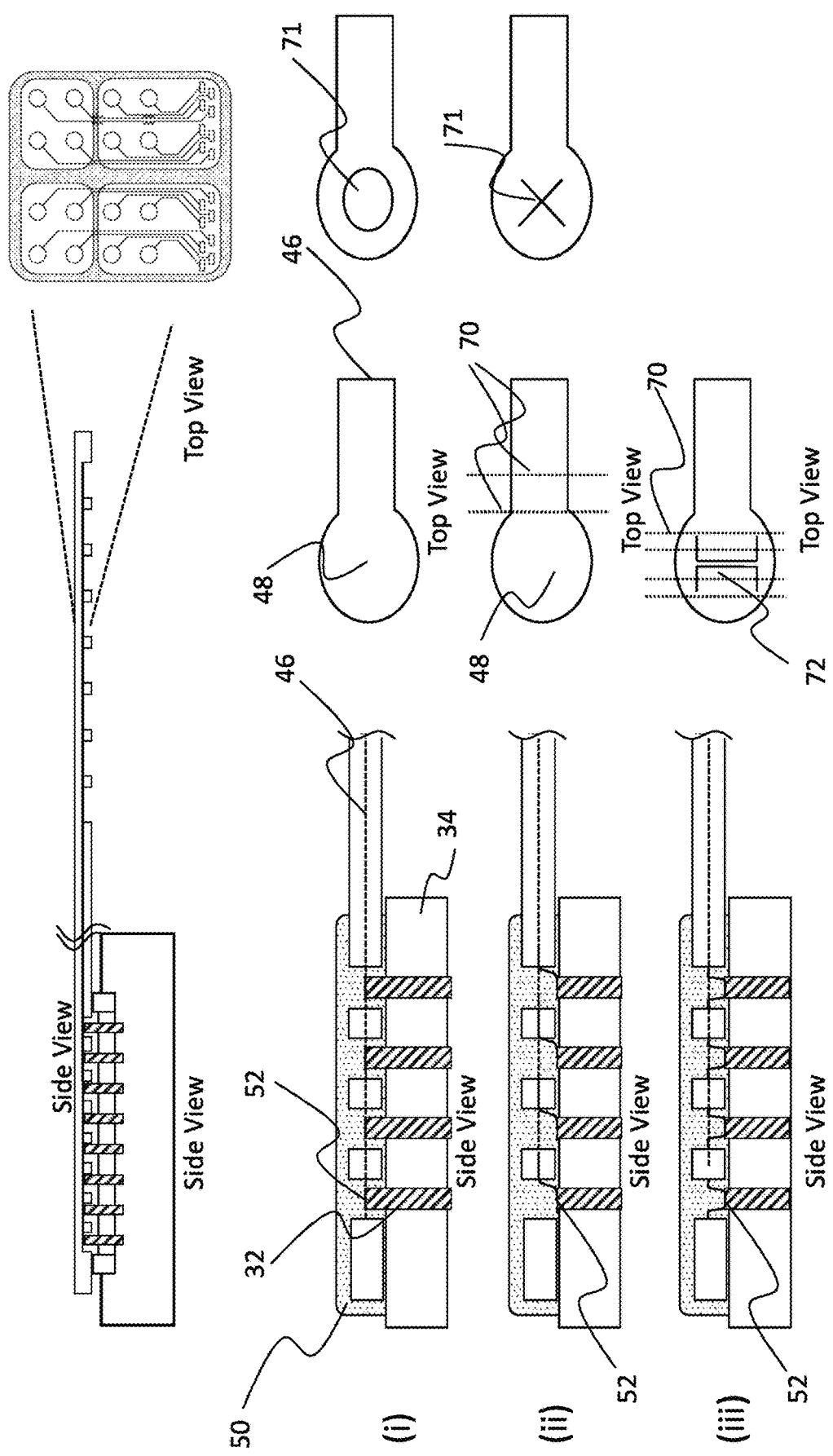
FIG. 18 schematically shows the continuous conductive elements and features such as connection pads and bending geometries that facilitate the creation of permanent bonds between the faces of (i) protruding hermetic feedthrough conductors and (ii, iii) non-protruding hermetic feedthrough conductors and the curved connection pads of the continuously conducting elements on the flexible, multi-contact electrode array in illustrative embodiments.

FIG. 18(*i*) graphically shows a process of forming permanent conductive bonds 52 between a hermetic enclosure with the protruding feedthrough conductors 32 and connection pads 48 on the continuously conducting elements 42 in illustrative embodiments. In another embodiment, FIG. 18(*ii*) depicts how folding lines 70 may be pressed using a fixture to shape the connection pads 48 of the continuously conducting elements such that they may extend towards the hermetic feedthrough faces which may be flush with the hermetic insulating substrate. After the conductors are closely coupled, the permanent bonds may be formed. In a similar fashion, FIG. 18(*iii*) depicts connection pads 48 with bonding flap features 72 which may be depressed to contact the hermetic feedthrough. Additionally, aperture features 71 may be created in the form of a circular hole, cross-cuts, spines, ridges, pinwheels, etc. After permanent bonds are formed, an insulating material 50 is formed around the exposed contacts to provide and isolated and water-tight bond at the interface.

Figure 19:
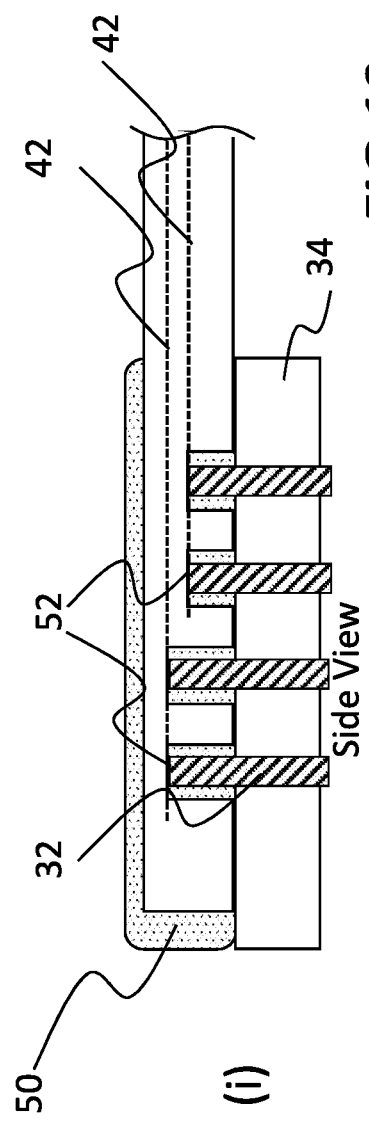
FIG. 19 schematically shows an embodiment of a flexible multi-contact electrode array with two-layers of continuously conducting elements with hermetic feedthrough conductors faces positioned at two spatial offset distances from the external surface of the insulating feedthrough substrate. Permanent bonds are created at the interface of the feedthrough faces and the continuous conducting element connection pads on two or more levels. An insulating material fills the voids.

FIG. 19 shows another embodiment of the invention in which the hermetic insulating substrate 34 has conductive feedthrough conductors 32 with faces that are two or more distances offset from the external insulating face. The flexible multi-contact electrode array 38 contains two embedded layers of continuous conductive elements 42. As shown in FIG. 19, the upper layer of continuous conducting elements 42 is bonded to the longer feedthrough and the lower layer of continuous conducting elements 42 is bonded to the shorter feedthrough array 32. Permanent bonds 52 (e.g., welded bonds) are formed using the methods previously described. An insulating material 50 is applied around the permanent bonds and exposed elements to provide an isolated and moisture proof bond. The embodiment shows two feedthrough heights and two continuous conductive elements, but two or more layers are also envisioned in various embodiments. An additional embodiment uses a combination of the above approaches such as two layers of continuously conductive elements with only a single pin offset distance.

Figure 20:
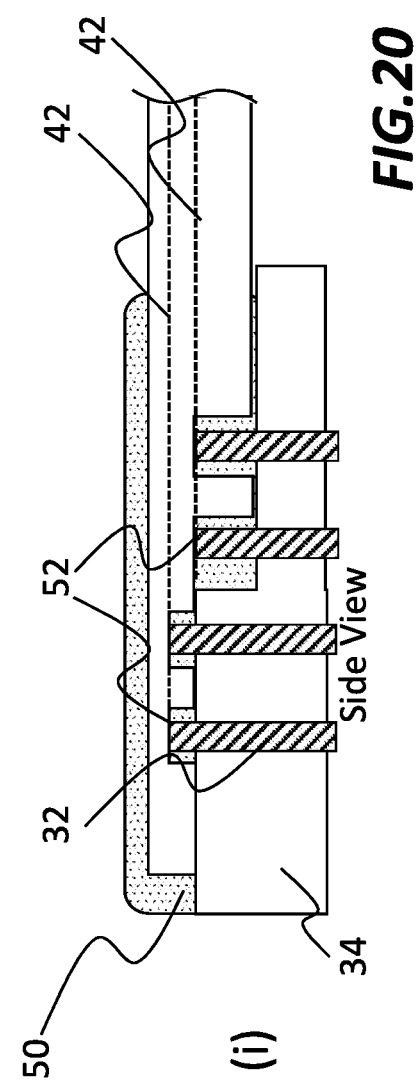
FIG. 20 schematically shows an embodiment of a flexible multi-contact electrode array with two-layers of continuously conducting elements with hermetic feedthrough insulating substrate in which the insulating substrate has two distinct thicknesses. Permanent bonds are created at the interface of the feedthrough faces and the continuous conducting element contact pads on two levels.

FIG. 20 shows another embodiment of the invention in which the hermetic insulating substrate 34 has one or more step heights or step changes on the external side. As depicted in FIG. 20, the hermetic insulating substrate has two thicknesses and the accompanying conductive feedthrough conductors 32 extend through the substrate. The flexible multi-contact electrode array 38 contains two embedded layers of continuous conductive elements 42. As shown in FIG. 19, the upper layer of continuous conducting elements 42 is bonded to the longer feedthrough and the lower layer of continuous conducting elements 42 is bonded to the shorter feedthrough array 32. Permanent bonds 52 preferably are formed using the methods previously described. An insulating material 50 is applied around the permanent bonds and exposed elements to provide an isolated and moisture proof bond. While this embodiment shows two, other embodiments may envision the insulating substrate with multiple thicknesses, feedthrough conductors 32 extending at multiple heights, and continuous conductive elements embedded in multiple layers. The insulating substrate may feature multiple step heights in thickness across the face of the substrate.

Figure 21:
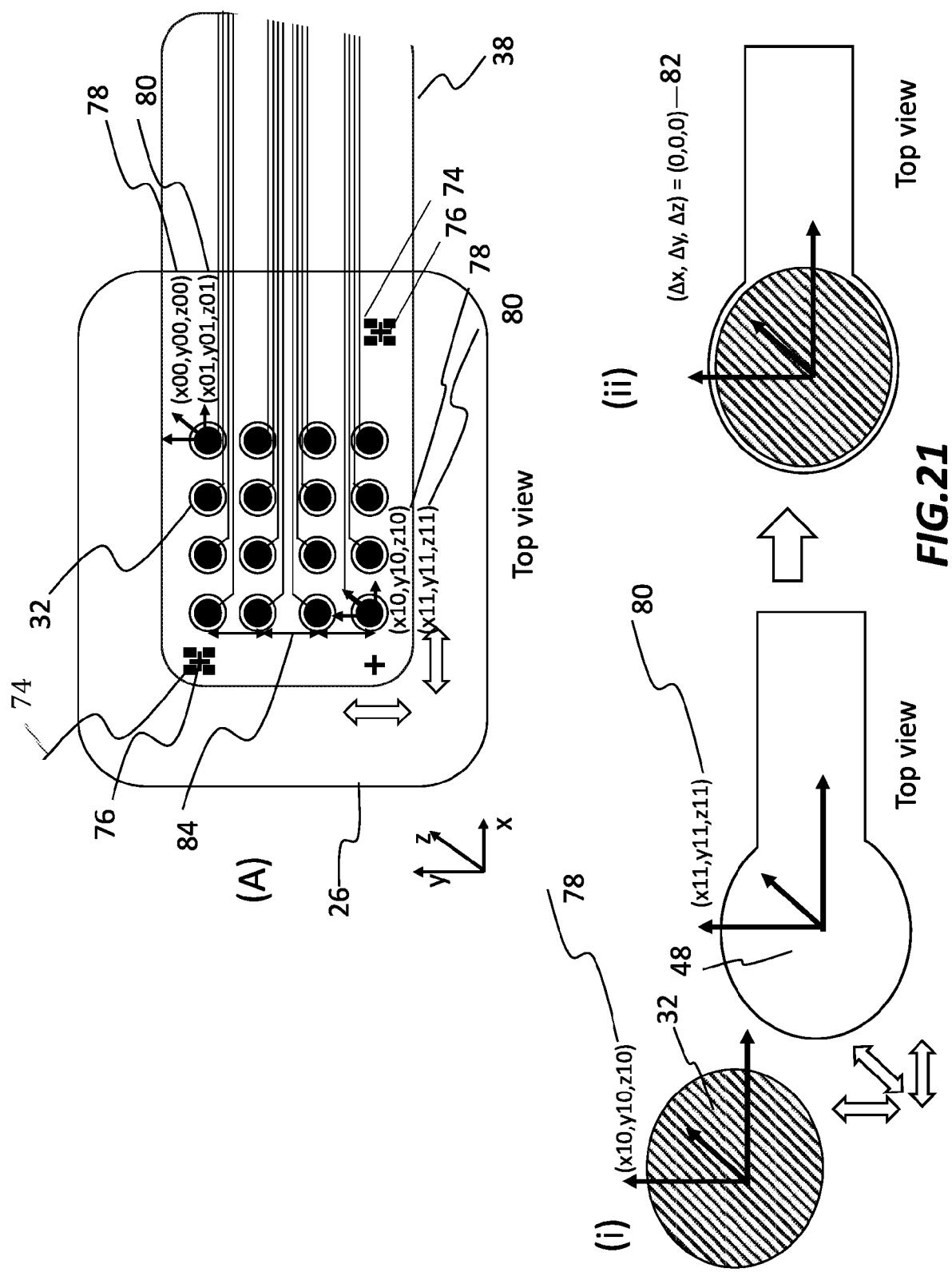
FIG. 21 illustrates an illustrative alignment and position finding process in which the x, y, z location of both the insulating feedthrough substrate and the multi-contact flexible therapy array are determined and the information is used to align and compress the connection pads above the feedthrough faces in preparation for permanent bonding.

FIG. 21 shows additional embodiments of the invention of the hermetically sealed enclosure 26, the flexible multi-contact electrode array 38 with continuously conducting elements containing connection pads 48, and the array of conductive hermetic feedthrough conductors 32. The electrode substrate in this embodiment has alignment features 74 while the insulating substrate containing the feedthrough conductors 32 also has alignment features 76. In one embodiment of the invention, the alignment features 74 and 76 may be used to position the hermetic feedthrough conductors 32 in an aligned fashion to the connection pads 48 on the flexible multi-contact electrode array 38. In another embodiment, the alignment marks or the connection pads 48 may be used as fiducials to establish a three-dimensional electrode position 80 and feedthrough assembly position 78. Additionally, the geometric distance 84 between feedthrough elements 32 and connection pads 48 may be used to inform the bonding process, such as providing location information for parallel or sequential bonding. In another embodiment, a sacrificial carrier 63 may be attached to the multi-contact electrode array 38 and features in the sacrificial carrier may be used to align to the hermetic feedthrough assembly.

Referring to FIG. 21(*i*), the coordinates 78 of the hermetic feedthrough conductors 32 can be obtained. In a similar fashion, the coordinates 80 of the connection pads 48 of the flexible multi-contact electrode array 38 may be identified. Using staging, vision, optical, or mechanical alignment methods, the difference in X, Y, Z, and θ can be used to align all elements of the array together. Referring to FIG. 21(*ii*), after the staging has performed the alignment, the hermetic feedthrough element 32 is preferentially centered beneath the contact pad 48 providing a minimized offset coordinate 82. Various methods are envisioned to determine the feedthrough positions including precision fixturing and known geometric offsets, alignment features for optical alignment, machine vision to identify the coordinates of critical features to establish position information, and other methods of computing relative position between the substrates.

Referring again to FIG. 21, the absolute position of the subassembly of aligned connection pads 48 and hermetic feedthrough conductors 32 preferably is positioned precisely to facilitate the bonding methods depicted in FIG. 17. Sequential permanent bonds may be performed using the resistance welding approaches, or optical welding may be performed (e.g., laser welding using a positioning stage or a mask-based laser welding system).

Figure 22:
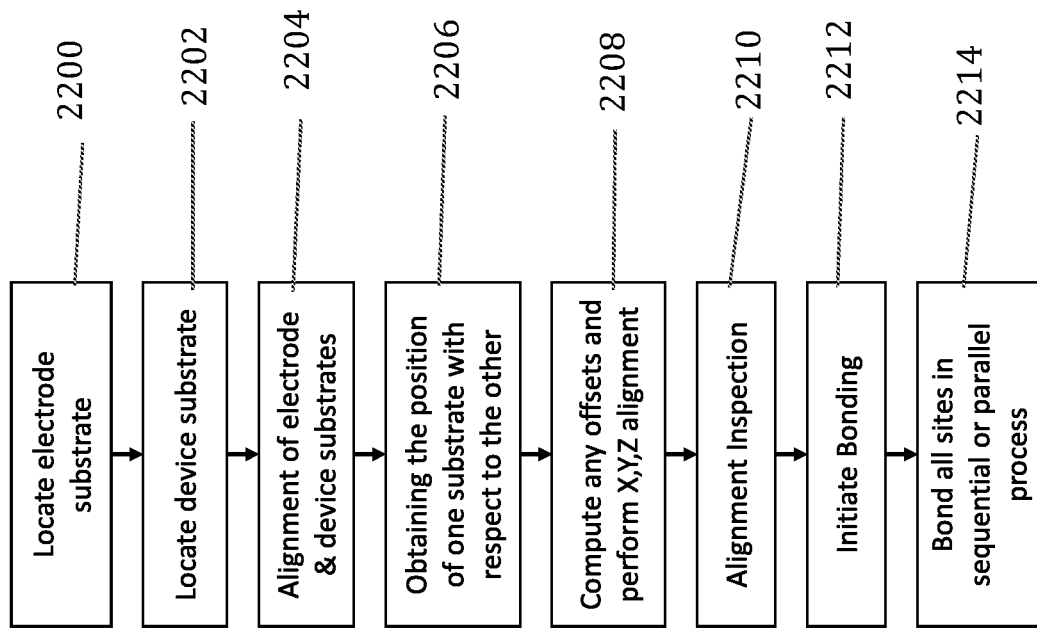
FIG. 22 illustrates a flowchart by which bonding may be accomplished in various embodiments. Substrates may be aligned together using relative or absolute positions before permanent bonding is performed.

FIG. 22 illustrates a bonding process performed by illustrative embodiments of the invention. It should be noted that this process is substantially simplified from a longer bonding process. Accordingly, the process may have many other steps, such as testing steps, which those skilled in the art may use. In addition, some of the steps may be performed in a different order than that shown, or at the same time. Those skilled in the art therefore can modify the process as appropriate. Moreover, as noted above and below, the materials and structures noted are but one of a wide variety of different materials and structures that may be used. Those skilled in the art can select the appropriate materials and structures depending upon the application and other constraints. Accordingly, discussion of specific materials and structures is not intended to limit all embodiments.

The process begins by locating and aligning the electrode substrate and device substrate (steps 2200-2204). Next, the process obtains the position of one substrate with regard to the other (step 2206), and computes offsets and performs alignment in three dimensions (e.g., X, Y, and Z), (step 2208). The process also compresses the conductive pads against the conductive feedthroughs. After conducting an alignment inspection in step 2210, the process initiates bonding (step 2212) and preferably bonds all sites either sequentially or in parallel (2214). As noted above, illustrative embodiments bond with a thermal bond that welds the relevant components together. As an example of this and related processes, to weld, the process unites the two components (e.g., feedthrough conductor 32 with pad 48) by liquifying and allowing their materials to flow together. As such, the welding process produces a spot or nugget formed between at least one pad 48 and at least one feedthrough conductor 32. Some alternative embodiments may weld using compression with or without prior heating. Illustrative embodiments thus use welding to melt the base materials, fusing the two components together.

The embodiments of the invention described above are intended to be merely exemplary; numerous variations and modifications will be apparent to those skilled in the art. Such variations and modifications are intended to be within the scope of the present invention as defined by any of the appended claims.

What is claimed is:

1. An implantable device comprising:
   a hermetically sealed enclosure;
   an electronic device within the hermetically sealed enclosure;
   a plurality of feedthrough conductors integrated with the hermetically sealed enclosure and exposed outside of the hermetically sealed enclosure, the plurality of feedthrough conductors being electrically connected with the electronic device within the hermetically sealed enclosure;
   a multi-contact electrode array comprising a flexible biocompatible substrate having a plurality of therapy contacts;
   a plurality of continuously conductive elements extending along the flexible substrate from the plurality of therapy contacts and terminating at a plurality of connection pads, at least one continuously conductive element being integral with at least one therapy contact and at least one connection pad to electrically couple the at least one therapy contact and the at least one connection pad, the continuously conductive elements being electrically isolated from one another,
   each continuously conductive element having an element thickness in a direction generally normal to the substrate, at least a portion of at least one of the continuously conductive elements having an element thickness of between 5 microns and 190 microns; and
   a plurality of welded couplings directly connecting at least one of the connection pads to at least one of the feedthrough conductors.

2. The implantable device as defined by claim 1 wherein the plurality of continuously conductive elements comprise a weldable biocompatible conductor including one or more of platinum, platinum-iridium, stainless steel, palladium, and rhodium.

3. The implantable device as defined by claim 1 wherein the therapy contacts, continuously conductive elements, and connection pads comprise a plurality of connection sets, each connection set comprising at least one therapy contact, at least one continuously conductive element, and at least one connection pad, each set being electrically isolated from other connection sets.

4. The implantable device as defined by claim 1 wherein the substrate comprises at least one insulating material having a modulus of elasticity of between 1 megapascal and 5 gigapascals.

5. The implantable device as defined by claim 1 wherein each welded coupling comprises a conductive joint formed from at least one pad and at least one feedthrough conductor, the at least one pad being in electrical contact with at least one continuously conductive element at the conductive joint.

6. The implantable device as defined by claim 1 wherein the insulating substrate has a plurality of layers of continuously conductive elements, therapy contacts, connection pads, and a plurality of conductive welded couplings.

7. The implantable device as defined by claim 1 wherein the hermetically sealed enclosure has a surface, the plurality of feedthrough conductors extending through and beyond the surface of the enclosure.

8. The implantable device as defined by claim 1 wherein the hermetically sealed enclosure has a surface, the plurality of feedthrough conductors being generally flush with the surface of the enclosure.

9. The implantable device as defined by claim 1 wherein the continuously conductive elements include metal traces integrated into the substrate.

10. The implantable device as defined by claim 1 wherein the plurality of therapy contacts comprises no fewer than 16 therapy contacts but no more than 72 therapy contacts.

11. The implantable device as defined by claim 1 wherein the substrate comprises insulating material configured to electrically insulate the plurality of continuously conductive elements.

12. The implantable device as defined by claim 1 wherein the electronic device has an interfacing portion to electrically couple with an implantable circuit.

13. The implantable device as defined by claim 1 further comprising a circuit operatively coupled with the hermetically sealed enclosure.

14. The implantable device as defined by claim 1 wherein the substrate is formed from one or more of silicone, polyurethane, silicone-polyurethane co-polymer, liquid crystal polymer, polyethylene terephthalate, silicone-polyurethane copolymer, parylene, or polyimide.

15. The implantable device as defined by claim 1 wherein the element thickness of each continuously conductive element is between 1 micron and 1125 microns.

16. The implantable device as defined by claim 1 further comprising an insulative underfill between adjacent continuous conducting elements.

17. An implantable device comprising:
a hermetically sealed enclosure;
an electronic device within the hermetically sealed enclosure;
feedthrough conductor means integrated with the hermetically sealed enclosure and exposed outside of the hermetically sealed enclosure, the feedthrough conductor means being in electrical communication with the electronic device within the hermetically sealed enclosure;
a multi-contact electrode array comprising a flexible biocompatible substrate having a plurality of therapy contacts; and
connection means extending along the flexible substrate from the plurality of therapy contacts and terminating at a plurality of connection pads, at least one connection means being integral with at least one therapy contact and at least one connection pad to electrically communicate the at least one therapy contact and the at least one connection pad, the connection means being electrically isolated from one another,
the connection means having an element thickness in a direction generally normal to the substrate, at least a portion of at least one of the connection means having an element thickness of between 5 microns and 490 microns,
a plurality of welded means directly connecting at least one of the connection pads to at least one of the feedthrough conductor means.

18. The implantable device as defined by claim 17 wherein the connection means comprise platinum or platinum-iridium.

19. The implantable device as defined by claim 17 wherein the therapy contacts, connection means, and connection pads comprise a plurality of connection sets, each connection set comprising at least one therapy contact, at least one connection means, and at least one connection pad, each set being electrically isolated from other connection sets.

20. The implantable device as defined by claim 17 wherein the connection means includes metal traces integrated into the substrate.

21. The implantable device as defined by claim 17 wherein the set of therapy contacts comprises no fewer than 16 therapy contacts but no more than 72 therapy contacts.

* * * * *